United States Patent [19]

Azuma et al.

[11] Patent Number: 4,845,264
[45] Date of Patent: Jul. 4, 1989

[54] PHENOXYCARBOXYLIC ACID AND HERBICIDE COMPRISING IT AS ACTIVE INGREDIENT

[75] Inventors: Shizuo Azuma; Toshiyuki Hiramatsu; Koji Nakagawa, all of Iwakuni; Yataro Ichikawa, Tokorozawa, all of Japan

[73] Assignee: Teijin Limited, Osaka, Japan

[21] Appl. No.: 162,727

[22] Filed: Mar. 1, 1988

[30] Foreign Application Priority Data

Mar. 5, 1987 [JP] Japan .................................. 48839
Sep. 25, 1987 [JP] Japan .................................. 239014

[51] Int. Cl.$^4$ ............................................. C07C 69/76
[52] U.S. Cl. ..................................... 560/053; 560/61; 560/62; 562/464; 562/471; 562/472; 564/169; 564/171; 564/175; 568/331; 558/389; 558/398; 71/86; 71/105; 71/108; 71/118

[58] Field of Search ................................. 560/53, 61, 62; 562/464, 471, 472; 564/169, 171, 175; 568/331; 558/389, 398; 71/86, 105, 108, 118

[56] References Cited

FOREIGN PATENT DOCUMENTS 0023392 2/1981 European Pat. Off. .

*Primary Examiner*—Paul J. Killos
*Attorney, Agent, or Firm*—Wenderoth, Lind & Ponack

[57] ABSTRACT

A novel phenoxycarboxylic acid of formula (I) is disclosed. The compound is effective as herbicide for eradicating broad-leaved weeds. A combination of the phenoxycarboxylic acid and a N-phosphonomethylglycine or a glufosinate which is known as a herbicide is very effective for eradicating both broad-leaved weeds and narrow-leaved weeds.

20 Claims, No Drawings

PHENOXYCARBOXYLIC ACID AND HERBICIDE COMPRISING IT AS ACTIVE INGREDIENT

This invention is a continuation-in-part application of U.S. patent application Ser. No. 116,736 abandoned filed November 4, 1987, abandoned which was in turn a continuation-in-part application of U.S. patent application Ser. No. 026,988 filed Mar. 17, 1987, now abandoned.

This invention relates to a phenoxy carboxylic acid and a herbicide comprising it as an active ingredient. More specifically, this invention pertains to phenoxy carboxylic acids which have selective herbicidal activity and selectively eradicate broad-leaved weeds without substantially harming the growth of narrow-leaved crop plants as well as broad-leaved crop plants.

Herbicides of the type which selectively kills broad-leaved weeds, typified by 2,4-dichlorophenoxyacetic acid, are known as selective herbicidally active compounds. The selectivity of the herbicidal activity of 2,4-dichlorophenoxyacetic acid is between narrow-leaved plants including crop plants and weeds and broad-leaved plants including crop plants and weeds. It is known that 2,4-dichlorophenoxyacetic acid has very little or no activity against narrowleaved plants [see, for example, Nature, Vol. 155, page 498 (1945)]. It is known on the other hand that compounds resulting from introduction of a chloro- or trifluoromethyl-substituted phenoxy group or a chloro- or trifluoromethyl-substituted pyridyloxy group into the aromatic group of the above compound have the activity of selectively killing narrow-leaved plants (see U.S. Pat. Nos. 4270948, 4309562, 4314069, 4332961 and 3954442, British Pat. No. 1,579,201, and Japanese Laid-Open Patent Publications Nos. 125626/1977 and 15825/1977). These compounds, however, also kill useful crops such as rice or corn.

U.S. Pat. No. 3,928,416 discloses that diphenyl ethers represented by the following formula

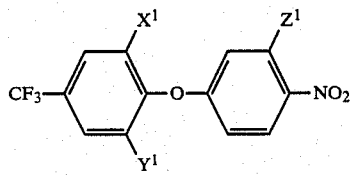

wherein $X^1$ is a hydrogen atom, a halogen atom, a trihalomethyl, a $C_1$–$C_4$ alkyl or cyano, $Y^1$ is a hydrogen atom, a halogen atom, or a trihalomethyl, and $Z^1$ is a hydroxy, an alkoxy, an alkyl, a halogen atom, an amino, a cyano, a carboxy, a carbalkoxy, —$CO_2R$, a carboxyalkyl —$R'CO_2H$, a carbaloxyalkyl —$R'CO_2R$, an alkanoyloxy —OCOR, a carbamoyloxy, —$OCONH_2$ —OCONHR or —$OCONR_2$, have herbicidal activity.

European Laid-Open Patent Publication No. 165,203 discloses benzoyloxyalkylphosphonic or phosphinic acids represented by the following formula

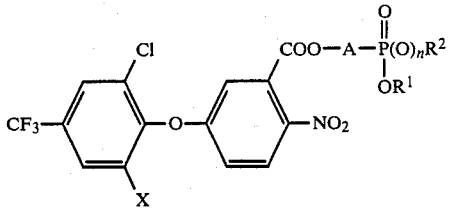

wherein X is H or Cl, n is 0 or 1, A is $C_1$–$C_3$ alkyl substituted by one or two $C_1$–$C_2$ alkyls and/or one or two phenyls, and $R^1$ and $R^2$, independently from each other, represent H or $C_1$–$C_4$ alkyl. Tables 2 to 4 of this patent document show that the above compounds show excellent effects against various weeds but cause unneglible phytotoxicity to the growth of wheat, corn, soybean, cotton or rice.

U.S. Pat. No. 4,364,767 discloses herbicidal compounds of the following formula

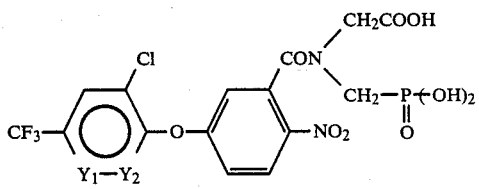

wherein $Y_1$ is N or CH, $Y_2$ is N or CH provided that $Y_1$ is not N when $Y_2$ is CH, and agronomically acceptable salts thereof. This U.S. Patent discloses no data showing the herbicidal activity of the above compounds.

U.S. Pat. No. 4,536,355 discloses a herbicide represented by the following formula

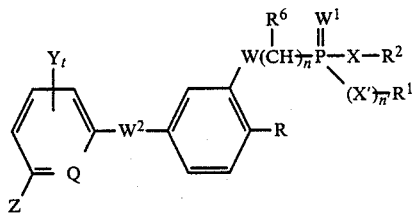

wherein R is, for example, nitro, n is 0 or 1, n' is 1, 2 or 3, $R^1$ is, for example, hydrogen, or lower alkyl, $R^2$ is, for example, hydrogen or lower alkyl, $R^6$ is, for example, hydrogen, or lower alkyl, Q is CH or N, W is oxygen, sulfur, sulfinyl, sulfonyl or $NR^5$ in which $R^5$ is hydrogen or lower alkyl, $W^1$ is oxygen or sulfur, $W^2$ is, for example, oxygen, each of X and X' is, for example, oxygen, each of Y and Z is, independently, hydrogen, lower alkyl, lower haloalkyl, halogen, lower alkoxy, lower haloalkoxy, cyano or nitro, and t is 1 or 2.

Japanese Patent Publication No. 34418/86 discloses a 2-phenoxy-5-trifluoromethyl pyridine represented by the following formula

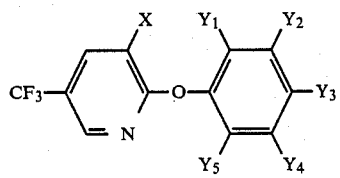

wherein X is a hydrogen or chlorine atom, $Y_1$ and $Y_5$ are a hydrogen or halogen atom, or a hydroxyl, nitro or amino group, $Y_2$ and $Y_4$ are a hydrogen or halogen atom, or hydroxyl, lower alkyl, lower alkoxyl, —COOR$_1$ (where R$_1$ is hydrogen, a cation lower alkyl or benzyl) or

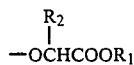

(where R$_1$ is defined as above,
R$_2$ is a hydrogen atom or a lower alkyl,
Y$_3$ is a hydrogen or halogen atom, or cyano, nitro, amino, acetylamino, —S(O)$_n$CH$_3$ (where n is an integer), —COOR$_1$ (where R$_1$ is defined as above) or

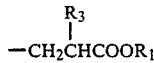

(where R$_1$ is defined as above and
R$_3$ is hydrogen or a halogen atom).

This patent document also discloses that the compounds are useful as an active ingredient of a medicine, or an intermediate thereof.

U.S. Pat. No. 4,227,914 discloses a herbicidally active phenoxy-alkyloxazolines represented by the formula

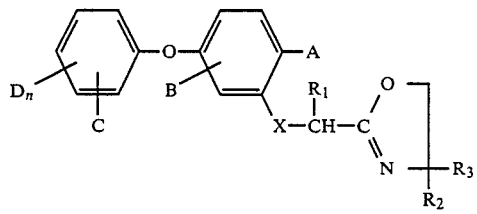

wherein
A is hydrogen, halogen, cyano, nitro and amido or thiamido radical,
B is hydrogen, C$_1$-C$_4$ alkyl,
C is halogen, cyano, nitro or trifluoromethyl, amido or thiamido,
D is halogen, cyano or nitro,
n is 0, 1 or 2,
R$_1$, R$_2$ and R$_3$, independently are hydrogen or C$_1$-C$_4$ alkyl and
X is oxygen, sulfur, sulfinyl or sulfonyl.

While, U.S. Pat. No. 3,799,758 discloses a N-phosphonomethylglycines of this invention are

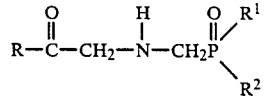

wherein R, R$^1$ and R$^2$ are independently selected from the group consisting of:

Halogen; —OH; —SH;

—NR$^4$R$^5$ wherein R$^4$ and R$^5$ are independently selected from the group consisting of hydrogen, alkyl and hydroxyalkyl having 1 through 4 carbon atoms, alkenyl having 2 through 4 carbon atoms, and R$^4$ and R$^5$ together with the nitrogen atom can form a heterocyclic ring; —OR$^3$ and —SR$^3$ wherein R$^3$ is selected from the group consisting of monovalent hydrocarbon groups, monovalent hydrocarbonoxyhydrocarbon groups each containing from 1 to 18 carbon atoms, halogenated monovalent hydrocarbon groups, halogenated monovalent hydrocarbonoxyhydrocarbon groups each containing from 1 to 18 carbon atoms and from 1 to 3 halogens,

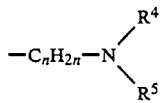

groups wherein n is from 1 to 4 and R$^4$ and R$^5$ are as above defined provided that no more than two of R, R$^1$ or R$^2$ can be —NR$^4$R$^5$, —OR$^3$ or —SR$^3$; and —OR$^6$ wherein R$^6$ is a salt-forming cation selected from the group consisting of cations of alkali metals, alkaline earth metals, copper, zinc, manganese, nickel, ammonium, organic ammonium, provided that when the organic group is aryl the ammonium salt is a primary amine salt, and mixtures of such salts, provided that when any one of R, R$^1$ or R$^2$ is halogen the others of R, R$^1$ or R$^2$ cannot be —OR$^6$, and further provided that no more than two of R, R$^1$ or R$^2$ are —OR$^6$ when R$^6$ is ammonium or orgnaic ammonium (see, U.S. Pat. Nos. 3,977,860, 4,405,531, 4,106,923 and 4,495,363, each of them is a division from the U.S. Pat. No. 3,799,758).

U.S. Pat. No. 3,853,530 discloses a compound represented by the formula

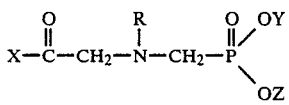

wherein:
R is selected from the group consisting of hydrogen, formyl, acetyl, benzoyl, nitrobenzoyl and chlorinated benzoyl;
Y and Z are each independently selected from the group consisting of hydrogen and lower alkyl;
X is selected from the group consisting of hydroxy, alkoxy and chloroalkoxy of up to 12 carbon atoms, lower alkenoxy, cyclohexyloxy, morpholino, pyrrolidinyl, piperidino and NHR'; and
R' is selected from the group consisting of hydrogen, lower alkyl and alkenyl, cyclohexyl, phenalkyl of up to 8 carbon atoms, phenyl, clorinated phenyl and anisyl; and certain salts of these compounds, which salts are selected from the group consisting of the Group I and II metals having an atomic number up to 30, hydrochloride, pyridine, ammonium, lower aliphatic hydrocarbon amine, lower alkanol amine and aniline.

The compound is useful for regulating the natural growth or development of plants (see, U.S. Pat. Nos. 3,988,142 and 4,025,332. U.S. Pat. No. 4,025,332 is a continuation-in-part of Ser. No. 510,923, U.S. Pat. No. 3,988,142 which is a continuation-in-part of Ser. No. 223,351, U.S. Pat. No. 3,853,530).

U.S. Pat. No. 4,168,963 discloses a herbicidal agent containing a compound of the general formula $$R_3-\overset{O}{\overset{\|}{C}}-\overset{R_5}{\underset{R_4-NH}{C}}-(CH_2)_2-\overset{X}{\overset{\|}{P}}\overset{R_1}{\underset{R_2}{\diagup}}\cdot(HY)_m$$

in which $R_1$ represents methyl, which may optionally be halogenated 1 to 3 times, preferably chlorinated, $R_2$ represents —OH, —SH, —OM or —SM (wherein M is the equivalent of an inorganic or organic base), $R_3$ represents
(a) —OH, —SH, —OM or —SM,
(b) ($C_1$–$C_{12}$)-alkoxy, ($C_3$–$C_8$)-cycloalkoxy, ($C_2$–$C_6$)-alkenyloxy, ($C_3$–$C_6$)-alkynyloxy, phenoxy, phenoxyphenoxy or benzyloxy as well as the corresponding thio analogs of these radicals, wherein the said groups may in turn be substituted by OH, halogen, $CF_3$, $NH_2$, $NO_2$, ($C_1$–$C_4$)-alkyl, ($C_1$–$C_4$)-alkoxy, carboxyl, ($C_1$–$C_6$)-alkoxycarbonyl, ($C_1$–$C_4$)-alkylamino, di-($C_1$–$C_4$)-alkylamino, piperidino, pyrrolidino, piperazino or morpholino,
(c) amino, ($C_1$–$C_4$)-alkylamino, di-($C_1$–$C_4$)-alkylamino, ($C_7$–$C_{10}$)-phenalkylamino, di-($C_7$–$C_{10}$)-phenalkylamino, wherein the said groups may in turn be substituted by OH, ($C_1$–$C_4$)-alkyl, ($C_1$–$C_4$)-alkylamino, di-($C_1$–$C_4$)-alkylamino, ($C_1$–$C_4$)-alkoxy, halogen or carboxyl; hydrazino, β-($C_1$–$C_4$)-alkylhydrazino, β,β-di-($C_1$–$C_4$)alkylhydrazino, ($C_1$–$C_{12}$)acyloxy, halogen-($C_1$–$C_{12}$)-acyloxy, piperidino, pyrrolidino, piperazino, morpholino or anilino, which is optionally substituted once or twice in the phenyl ring by ($C_1$–$C_4$)-alkyl, F, Cl, Br, $NO_2$, OH, $CCl_3$, $CF_3$, ($C_1$–$C_4$)-alkylamino, di-($C_1$–$C_4$)-alkylamino, ($C_1$–$C_4$)-alkoxy, phenoxy or phenylamino, $R_4$ represents hydrogen, ($C_1$–$C_4$)-acyl, halogen-($C_1$–$C_4$)-acyl, benzoyl or radicals of the formula

—C(X)$NR_6R_7$ $R_5$ represents hydrogen or ($C_1$–$C_4$)-alkyl,
$R_6$ represents hydrogen or ($C_1$–$C_4$)-alkyl,
$R_7$ represents hydrogen, ($C_1$–$C_4$)-alkyl or phenyl, which is optionally substituted in the phenyl ring, preferably substituted once or twice, by ($C_1$–$C_4$)-alkyl, F, Cl, Br, $NO_2$, $CCl_3$, $CF_3$,
X represents oxygen or sulfur,
Y represents the anion of an inorganic or organic acid having a dissociation constant $>10^{-3}$,
m represents 0, ½ or 1.

It is an object of this invention to provide a novel phenoxy carboxylic acid.

Another object of this invention is to provide a selective herbicide showing selective herbicidal activity.

Another object of this invention is to provide a selective herbicide which selectively kills broad-leaved weeds without substantially inhibiting the growth of narrow-leaved plants and substantially affecting broad-leaved useful plants.

Another object of this invention is to provide a selective compound which eradicates broad-leaved weeds without substantially causing phytotoxicity to useful crops, for example broad-leaved crops such as soybean, cotton, sunflower and beet and narrow-leaved crops such as rice, corn and wheat, and therefore without substantially inhibiting the growth of these useful crops; and a herbicide containing the above compound.

Another object of this invention is to provide a compound which kills many broad-leaved plants or inhibit their growth without causing substantial phytotoxicity to narrow-leaved crops such as rice, corn and wheat and various broad-leaved crops, and therefore when applied to a locus where the aforesaid useful crops and hazardous weeds grow together, can create a condition in which the useful crops easily grow beyond the growth of the weeds.

Another object of this invention is to provide a selective herbicide applicable by foliar spraying and soil treatment, which can kill, or inhibit the growth of, weeds by application to their foliage, and also can inhibit the emergence of weeds without substantially inhibiting the emergence of useful crops by application to the soil before emergence.

Another object of this invention is to provide a selective herbicide which has low toxicity to animals and fish and remains little in the soil.

Another object of this invention is to provide a method of eradicating weeds by using the aforesaid compounds or herbicides of this invention.

Another object of this invention is to provide a herbicidal composition and method in which by using the novel phenoxycarboxylic acid in combination with a N-phosphonomethylglycine known per se, both narrow-leaved weeds and broad-leaved weeds can be eradicated in relatively low dosages while taking advantages of the herbicidal properties of these individual herbicidal ingredients.

Another object of this invention is to provide a herbicidal composition comprising the novel phenoxycarboxylic acid of this invention in combination with known glufosinate, and a method of eradicating annual narrow-leaved weeds and broad-leaved weeds by using the composition in relatively low dosages and taking advantages of the herbicidal properties of these ingredients.

Further objects of this invention along with its advantages will become apparent from the following description.

According to this invention, the above objects and advantages of the invention are achieved by a phenoxycarboxylic acid represented by the following formula (I)

$$X-\underset{}{\overset{Y}{\text{-phenyl-}}}-O-\text{phenyl-}\underset{\overset{|}{R^3}}{\overset{COR^1}{\underset{OCH-COR^2}{}}} \quad (I)$$

wherein X and Y are identical or different and each represents a hydrogen atom, a halogen atom, —$CF_3$, or an alkyl group having 1 to 5 carbon atoms; $R^1$ and $R^2$ are identical or different and each represents an alkyl group having 1 to 5 carbon atoms which may be substituted by an alkoxycarbonyl group having 2 to 6 carbon atoms, a cyano group, an alkylthio group having 1 to 5 carbon atoms which may be substituted by an alkoxycarbonyl group having 2 to 6 carbon atoms, a group of the formula —OR$^4$ in which R$^4$ is a hydrogen atom, an alkyl group having 1 to 5 carbon atoms, or a trifluoroalkyl group, or a group of the formula

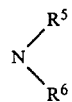

in which R$^5$ and R$^6$ are identical or different and each represents a hydrogen atom, an alkyl group having 1 to 5 carbon atoms, an alkylsulfonyl group having 1 to 5 carbon atoms, or a phenyl group; and R$^3$ represents a hydrogen atom or an alkyl group having 1 to 5 carbon atoms, or a salt of said compound in which R$^4$ is a hydrogen atom.

In formula (I), X and Y are identical or different, and each represents a hydrogen atom, a halogen atom, CF$_3$ or an alkyl group having 1 to 5 carbon atoms. The halogen atom is, for example, fluorine, chlorine or bromine. The alkyl group having 1 to 5 carbon atoms may be linear or branched, and includes, for example, methyl, ethyl, n-propyl, iso-propyl, n-butyl, sec-butyl, iso-butyl, t-butyl and n-pentyl.

In formula (I), at least one of X and Y is preferably a halogen atom, CF$_3$ or an alkyl group having 1 to 5 carbon atoms.

In formula (I), X is especially preferably CF$_3$, and Y is especially preferably a halogen atom.

In formula (I), R$^1$ and R$^2$ are identical or different and each represents an alkyl group having 1 to 5 carbon atoms which may be substituted by an alkoxycarbonyl group having 2 to 6 carbon atoms, a cyano group, an alkylthio group having 1 to 5 carbon atoms which may be substituted by an alkoxycarbonyl group having 2 to 6 carbon atoms, a group of the formula —OR$^4$ or a group of the formula

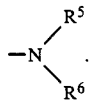

R$^4$ is a hydrogen atom, an alkyl group having 1 to 5 carbon atoms, or a trifluoroalkyl group. R$^5$ and R$^6$ are identical or different, and each represents a hydrogen aotm, an group having 1 to 5 carbon atoms, an alkylsulfonyl group having 1 to 5 carbon atoms, or a phenyl group.

R$^3$ is a hydrogen atom or an alkyl group having 1 to 5 carbon atoms.

The alkyl group having 1 to 5 carbon atoms for R$^1$, R$^2$, R$^3$, R$^4$, R$^5$ and R$^6$ may be the same as those alkyl group which are given hereinabove with regard to X and Y.

Examples of the alkylthio group having 1 to 5 carbon atoms for R$^1$ and R$^2$ are methylthio, ethylthio, n-propylthio, butylthio and pentylthio groups.

Examples of the alkylsulfonyl groups having 1 to 5 carbon atoms for R$^5$ and R$^6$ are methylsulfonyl, ethylsulfonyl, propylsulfonyl, butylsulfonyl and pentylsulfonyl groups.

Examples of the trifluoroalkyl groups having 1 to 5 carbon atoms for R$^4$ are trifluoromethyl and trifluoroethyl groups.

Preferred R$^1$ and R$^2$ groups in formula (I) are the groups OR$^4$ in which R$^4$ represents an alkyl group having 1 to 5 carbon atoms or a trifluoroalkyl group.

R$^3$ is preferably an alkyl group having 1 to 5 carbon atoms.

Examples of the phenoxycarboxylic acids of formula (I) are given below.

(1) ethyl 2-[2-methoxycarbonyl-5-(2-chloro-4-trifluoromethylphenoxy)]phenoxypropionate.
(2) methyl 2-[2-methoxycarbonyl-5-(2-chloro-4-trifluoromethylphenoxy)]phenoxypropionate.
(3) ethyl 2-[2-carboxy-5-(2-chloro-4-trifluoromethylphenoxy)]phenoxypropionate.
(4) 2′,2′,2′-trifluoroethyl 2-[2-carboxy-5-(2-chloro-4-trifluoromethylphenoxy)]phenoxypropionate.
(5) buthyl 2-[2-butoxycarbonyl-5-(2-chloro-4-trifluoromethylphenoxy)]phenoxypropionate.
(6) ethyl 2-[2-carbamoyl-5-(2-chloro-4-trifluoromethylphenoxy)]phenoxypropionate.
(7) 2′,2′,2′-trifluoroethyl 2-[2-(2,2,2-trifluoroethoxycarbonyl)-5-(2-chloro-4-trifluoromethylphenoxy)]phenoxypropionate.
(8) ethyl 2-[2-methoxycarbonyl-5-(4-trifluoromethylphenoxy)]phenoxypropionate.
(9) methyl [2-methoxycarbonyl-5-(2-chloro-4-trifluoromethylphenoxy)]phenoxyacetate.
(10) ethyl [2-methoxycarbonyl-5-(2-chloro-4-trifluoromethylphenoxy)]phenoxyacetate.
(11) methyl 2-[2-methoxycarbonyl-5-(2,4-dichlorophenoxy)]phenoxypropionate.
(12) ethyl 2-[2-methoxycarbonyl-5-(2,4-dichlorophenoxy)]phenoxypropionate.
(13) N-2-[2-methoxycarbonyl-5-(2-chloro-4-trifluoromethylphenoxy)]phenoxypropionyl-methanesulfonamide.
(14) ethyl 2-[2-methanesulfonamidocarbonyl-5-(2-chloro-4-trifluoromethylphenoxy)]phenoxypropionate.
(15) ethyl 2-[2-(N-iso-propylcarbamoyl)-5-(2-chloro-4-trifluoromethylphenoxy)]phenoxypropionate.
(16) ethyl 2-[2-(N,N-diethylcarbamoyl)-5-(2-chloro-4-trifluoromethylphenoxy)]phenoxypropionate.
(17) N-2-[2-methoxycarbonyl-5-(2,4-dichlorophenoxy)]-phenoxypropionyl-methanesulfonamide.
(18) N-2-[2-n-butoxycarbonyl-5-(2-chloro-4-trifluoromethylphenoxy)]phenoxypropionyl-methanesulfonamide.
(19) S-methyl 2-[2-methoxycarbonyl-5-(2-chloro-4-trifluoromethylphenoxy)]phenoxypropanethioate.
(20) methyl 2-[2-(methylthio)carbonyl-5-(2-chloro-4-trifluoromethylphenoxy)]phenoxypropionate.
(21) S-ethoxycarbonylmethyl 2-[2-methoxycarbonyl-5-(2-chloro-4-trifluoromethylphenoxy)]phenoxypropanethioate.
(22) methyl 2-[2-(ethoxycarbonylmethylthio)carbonyl-5-(2-chloro-4-trifluoromethylphenoxy)]phenoxypropionate.
(23) methyl 2-[2-(N-phenylcarbamoyl)-5-(2-chloro-4-trifluoromethylphenoxy)]phenoxypropionate.
(24) 2′,2′,2′-trifluoroethyl 2-[2-methoxycarbonyl-5-(2-chloro-4-trifluoromethylphenoxy)]phenoxypropionate.
(25) methyl 2-[2-(2,2,2-trifluoroethoxycarbonyl)-5-(2-chloro-4-trifluoromethylphenoxy)]phenoxypropionate.
(26) methyl 2-[2-cyanocarbonyl-5-(2-chloro-4-trifluoromethylphenoxy)]phenoxypropionate.

(27) methyl 2-[2-methylcarbonyl-5-(2-chloro-4-trifluoromethylphenoxy)]phenoxypropionate.

(28) ethyl 2-[2-methylcarbonyl-5-(2-chloro-4-trifluoromethylphenoxy)]phenoxypropionate.

(29) methyl 2-[2-(1-methoxycarbonyl)ethoxycarbonyl-4-trifluoromethylphenoxy)]phenoxypropionate.

(30) n-butyl 2-[2-methoxycarbonyl-5-(2-chloro-4-trifluoromethylphenoxy)]phenoxypropionate.

(31) N-isopropyl-2-[2-methoxycarbonyl-5-(2-chloro-4-trifluoromethylphenoxy)]phenoxypropionamide.

The compound of formula (I) can be produced, for example, by processes shown by the following reaction schemes (A) and (B).

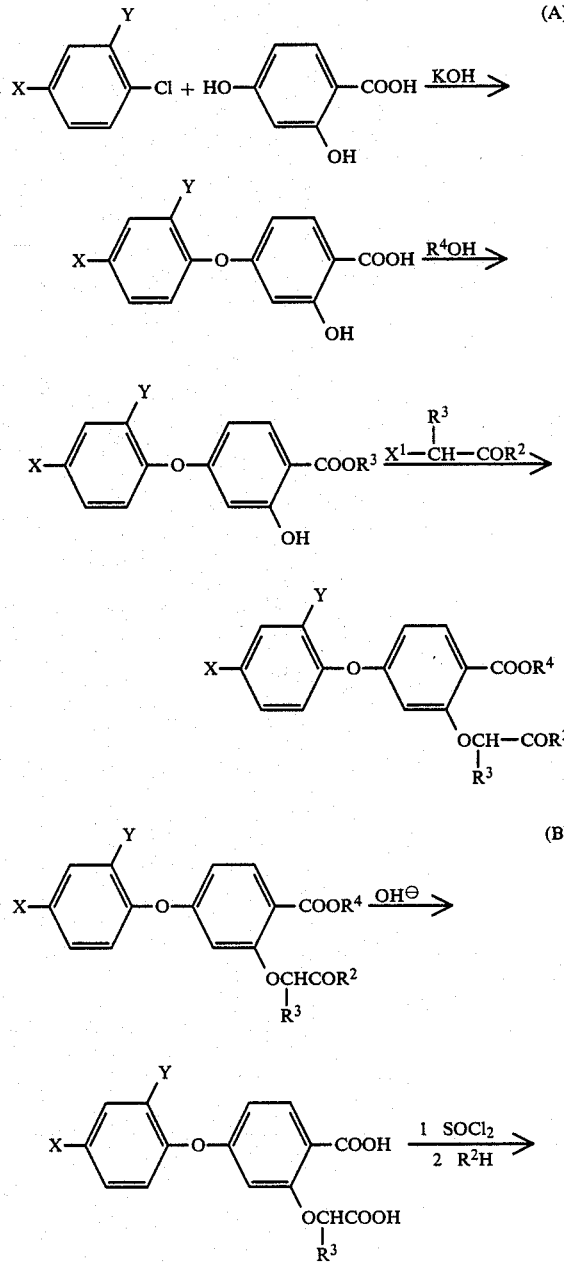

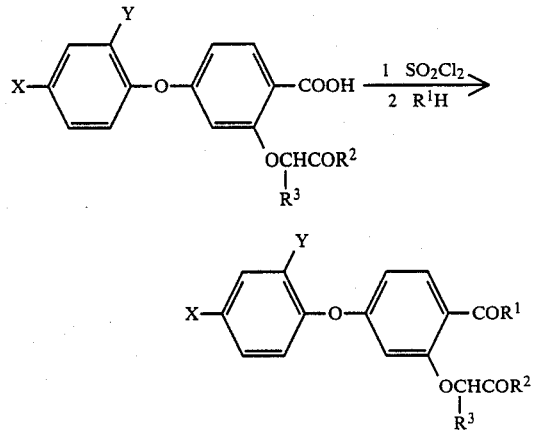

In Reaction Schemes (A) and (B), X, Y, $R^1$, $R^2$, $R^3$ and $R^4$ are the same as defined hereinabove.

The compounds of formula (I) provided by this invention show selective herbicidal activity, and particularly have the marked property of selectively killing broad-leaved weeds without substantially inhibiting the growth of narrow-leaved plants and substantially affecting useful broad-leaved plants.

Accordingly, the present invention also provides a herbicide comprising the phenoxy carboxylic acid of formula (I) as a herbicidally active ingredient.

The compounds of formula (I) provided by this invention can also be applied to seeds of plants, and to plants in various growth stages through foliage or roots. In other words, the compounds of this invention, either as such or as a composition, are applied to plants whose growth is to be inhibited, namely plants whose metabolism is to be regulated, seeds of such plants, a locus where such plants are growing, or a locus where the growth of such plants is anticipated, in amounts sufficient to regulate the metabolism of the plants.

The metabolism of plants can be regulated by applying the compounds of this invention at a rate of 0.01 g to 2 kg, preferably 0.02 g to 10 kg, especially preferably 0.05 g to 2 kg, per hectare.

When it is desired to inhibit the growth of, or eradicate, hazardous plants by the compounds of this invention, the compounds, either as such or as a composition, can be applied directly to the plants or their seeds or to the soil in amounts sufficient to inhibit the growth of, or eradicate, the plants in a locus where beneficial plants or their seeds and the hazardous plants or their seeds are growing together or are likely to grow together.

The hazardous plants may be defined as plants which come into an environment created by man, such as a paddy or an upland farm, from the surrounding nature, and grow there and which are considered by man to be useless in that environment or do harm to it. Such hazardous plants are generally called weeds. Examples of the weeds to which the compounds of this invention are to be applied are shown below.

Amaranthaceae
  Amaranthus retroflexas, and
  Amaranthus lividus.
Convolvulaceae
  Ipomoea purpurea, and
  Cuscuta japonica.
Polygonaceae
  Polygonum convolvulus, Polygonum hydropiper, and
Polygonum lapathifolium.
Chenopodiaceae
Chenopodium album,
Chenopodium album var. centrorubrum, and
Chenopodium ficifolium.
Portulacaceae
Portulaca oleracea.
Leguminosae
Desmodium tortuosum.
Malvaceae
Abutilon theophrasti, and
Sida spinosa.
Solanaceae
Solanum nigrum, and
Datula stramonium.
Compositae
Erigeron annuus,
Ambrosia artemisiaefolia var. elator.,
Xanthium strumarium, and
Cirsium arvense var. etosum.

The beneficial plants in the above case are, for example, plants producing cereals, and lawns. Since the compounds of this invention exert little or no adverse effect on the growth of not only various narrow-leaved plants such as rice, corn and wheat but also broad-leaved plants such as soybean and cotton, they are very suitable for application to paddies and upland farms for cultivating these plants. By applying the compounds of this invention to a locus where lawns are growing, the emergence and growth of weeds can be inhibited.

In some cases, it is desirable to apply the compounds of this invention while hazardous plants do not grow so much, particularly while the height of the hazardous plants is lower, or a little bit higher, than the height of beneficial plants.

When weeds are to be eradicated by using the compounds of this invention, the compounds can be applied either as such or as a composition to weeds to be eradicated, their seeds, or a locus where such weeds are growing, or are likely to grow, for example in a crop cultivating area, in amounts sufficient for eradication.

The herbicide of this invention shows a very good effect against broad-leaved weeds. When used in dosages which exhibit this effect, the herbicide does not substantially injure the aforesaid useful crops.

Among the compounds of formula (I) provided by this invention, preferred compounds having especially superior selective herbicidal activity are reprsented by the following formula (I)-1

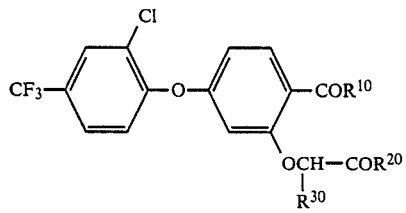
(I)-1 wherein
$R^{10}$ represents, $-CH_3$, $-OCH_3$ or $-OC_2H_5$,
$R^{20}$ represents $-OCH_3$, $-OC_2H_5$, $-SCH_3$ or $-SCH_2COOC_2H_5$
$R^{30}$ represents H or $-CH_3$.

The compounds of this invention can be used in usual formulations such as a solution, an emulsifiable concentrate, a suspension, a dust, a paste or granules.

Such formulations are prepared by using at least one agriculturally acceptable diluent. Examples include solid carriers such as talc, bentonite, clay, kaolin, diatomaceous earth, white carbon, vermiculite, slaked lime, ammonium sulfate and urea; liquid carriers such as water, alcohols, dioxane, acetone, xylene, cyclohexane, methylnaphthalene, dimethylformamide, N-methylpyrrolidone, dimethyl sulfoxide, cyclohexanone, methyl ethyl ketone and methyl isobutyl ketone; surface-active agents, emulsifiers or dispersants such as alkylsulfuric acid esters, alkylsulfonic acid salts, ligninsulfonic acid salts, polyoxyethylene glycol ethers, polyoxyethylene alkylaryl ethers, polyoxyethylene sorbitan monoalkylates and dinaphthylmethanedisulfonic acid salts; and various adjuvants such as carboxylmethyl cellulose and gum arabic.

For example, such a formulation can be prepared by mixing the compound of this invention with the aforesaid carrier and/or emulslifier, etc.

The compound of this invention may be present in a proportion of usually 0.01 to 99% by weight, preferably 0.1 to 95% by weight, in the formulation.

The compound of this invention, as such or in admixture with another active compound or as the aforesaid formulation, can be applied to plants by usual methods such as spraying, atomizing, or dusting.

The compound of formula (I) provided by this invention may be used in combination with various herbicidal compounds known per se. The compound (I) of this invention may be used together with a compound having excellent herbicidal activity against narrow-leaved weeds so that it may exhibit sufficient herbicidal activity selectively against broad-leaved weeds. Thus, there can be obtained a herbicidal composition which is effective against both broad-leaved weeds and narrow-leaved weeds.

Accordingly, the present invention secondly provide a herbicidal composition comprising as a herbicidal ingredient a combination of herbicidally effective amounts of the compound of formula (I) and a compound represented by the following formula (II)

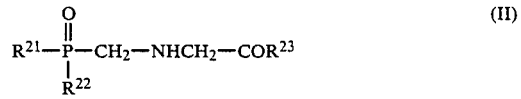
(II)

wherein $R^{21}$ and $R^{22}$ are identical or different and each represents $-OH$ or a group of the formula $-OR^{24}$, $R^{23}$ represents $-OH$, a group of the formula $-OR^{24}$ or a group of the formula $-NR^{25}R^{26}$ in which $R^{24}$ is an alkyl group having 1 to 5 carbon atoms, a cyclohexyl group, a haloalkyl group having 1 to 5 carbon atoms, an alkenyl group having 2 to 5 carbon atoms or an alkoxyalkyl, haloalkoxy-alkyl or alkoxy-alkoxy-alkyl group in which each of the alkoxy, haloalkoxy and alkyl moieties has 1 to 5 carbon atoms, or a phenoxy group, $R^{25}$ and $R^{26}$ are identical or different and each represents a hydrogen atom, an alkyl group having 1 to 5 carbon atoms, a hydroxyalkyl group having 1 to 5 carbon atoms, an alkenyl group having 2 to 5 carbon atoms and, $R^{25}$ and $R^{26}$, taken together with the nitrogen atom to which they are attached, form a morpholino, piperidino or pyrrolidino group, or an acid addition salt thereof or a salt thereof with a base, and a carrier and/or a surfactant.

In formula (II) above, $R^{21}$ and $R^{22}$ are identical or different and each represents —OH or a group of the formula —$OR^{24}$.

$R^{23}$ represents —OH, a group of the formula —$OR^{24}$ or a group of the formula —$NR^{25}R^{26}$.

$R^{24}$ represents an alkyl group having 1 to 5 carbon atoms, a cyclohexyl group, a haloalkyl group having 1 to 5 carbon atoms, an alkenyl group having 2 to 5 carbon atoms, or an alkoxy-alkyl, haloalkoxy-alkyl or alkoxy-alkoxy-alkyl group in which each of the alkoxy, haloalkoxy and alkyl moieties has 1 to 5 carbon atoms, or a phenoxy group. $R^{25}$ and $R^{26}$ are identical or different and each represents a hydrogen atom, an alkyl group having 1 to 5 carbon atoms, a hydroxyalkyl group having 1 to 5 carbon atoms, an alkenyl group having 2 to 5 carbon atoms, and $R^{25}$ and $R^{26}$, together with the nitrogen atom to which they are attached, form a morpholino, piperidino or pyrrolidino group.

Examples of the alkyl group for $R^{24}$, $R^{25}$ and $R^{26}$ may be the same as those given hereinabove with regard to X and Y in formula (I).

Examples of the haloalkyl group having 1 to 5 carbon atoms for $R^{24}$ include halomethyl, haloethyl, dihaloethyl, halopropyl, halobutyl, and halopentyl groups. The halo may, for example be, fluorine, chlorine or bromine.

Examples of the alkenyl group having 2 to 5 carbon atoms for $R^{24}$, $R^{25}$ and $R^{26}$ include vinyl, propenyl, butenyl and pentenyl groups.

Examples of preferred alkoxy-alkyl groups for $R^{24}$ are methoxyethyl and ethoxyethyl groups. Examples of preferred haloalkoxy-alkyl groups for $R^{24}$ are chloroethoxyethyl and chloromethoxyethyl groups.

Examples of preferred alkoxy-alkoxy-alkyl groups for $R^{24}$ are methoxyethoxyethyl and ethoxyethoxyethyl groups.

Examples of preferred hydroxyalkyl groups having 1 to 5 carbon atoms for $R^{25}$ and $R^{26}$ are hydroxymethyl, hydroxyethyl and omega-hydroxypentyl groups.

Compounds of formula (II) are disclosed in the above-cited U.S. Pat. No. 3,799,758 and are believed to be novel per se.

The compound of formula (II) may be used in the form of its acid addition salt or its salt with a base in the composition of this invention.

Strong acids having a pKa of, for example, not more than 2.5 are preferred as acids for forming the acid addition salts. Examples include hydrochloric acid, sulfuric acid, phosphoric acid, trifluoroacetic acid and trichloroacetic acid. The acid addition salts are believed to be formed at the secondary amino group in the molecule of formula (II).

The salt with a base is formed, for example, as a salt with a cation such as an alkali metal, an alkaline earth metal, copper, zinc, ammonium or an organic ammonium when at least one of $R^{21}$, $R^{22}$ and $R^{23}$ represents —OH.

The alkali metal represents, for example, lithium, sodium and potassium, and the alkaline earth metal represents, for example, magnesium and calcium.

The organic ammonium salt is produced from an organic amine having a low molecular weight of not more than about 300.

Examples of the organic amine include alkylamines, alkylenepolyamines and alkanolamines, such as methylamine, ethylamine, n-propylamine, isopropylamine, n-butylamine, isobutylamine, sec-butylamine, n-amylamine, iso-amylamine, hexylamine, heptylamine, octylamine, nonylamine, decylamine, undecylamine, dodecylamine, tridecylamine, tetradecylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-amylamine, diisoamylamine, dihexylamine, di-heptylamine, dioctylamine, trimethyleneamine, triethylamine, tri-n-propylamine, triisopropylamine, tri-n-butylamine, triisobutylamine, tri-sec-butylamine, tri-n-amylamine, ethanolamine, n-propanolamine, isopropanolamine, diethanolamine, N,N-diethylethanolamine, N-ethylpropanolamine, N-butylethanolamine, allylamine, n-butenyl-2-amine, n-pentenyl-2-amine, 2,3-dimethylbutenyl-2-amine, diphenyl-dimethylbutenyl-2-amine, dibutenyl-2-amine, n-hexenyl-2-amine and propylenediamine; primary arylamines such as aniline, methoxyaniline, ethoxyaniline, o-, m-, or p-toluidine, phenylenediamine, 2,4,5-tribromoaniline, benzidine, naphthylamine, and o-, m- or p-chloroaniline; and heterocyclic amines such as pyridine, morpholine, piperidine, pyrrolidine, indoline and azepine.

Preferred compounds of formula (II) are those in which one or two of $R^{21}$, $R^{22}$ and $R^{23}$ are —OH, —OH salt or —$OR^{24}$, and the remainder of $R^{21}$, $R^{22}$ and $R^{23}$ is —OH or its salt.

There can also be cited compounds of formula (II) in which one or two of $R^{21}$, $R^{22}$ and $R^{23}$ are salts of —OH, and the remainder of $R^{21}$, $R^{22}$ and $R^{23}$ is —OH. Examples of the salts of —OH are ammonium or organic ammonium salts (in which the organic ammonium group is selected from monoalkylammonium, dialkylammonium, trialkylammonium, monoalkenylammonium, dialkenylammonium, trialkenylammonium, monoalkynylammonium, dialkynylammonium, trialkynylammonium, monoalkanolammonium, dialkanolammonium, trialkanolammonium, heterocyclic ammonium and arylammonium, and contains 1 to 18 carbon atoms.

The salts of the compounds of formula (II) with acids or bases can be produced by methods known per se from the compounds of formula (II) with the acids or bases.

Examples of the compounds of formula (II) and their acid addition salts or their salts with bases are shown below.

(51) N-phosphonomethylglycine.
(52) sodium N-phosphonodimethylglycine.
(53) N-phosphonomethylglycine ammonium salt.
(54) monohydrate calcium salt of N-phosphonomethylglycine.
(55) magnesium salt of N-phosphonomethylglycine.
(56) potassium salt of N-phosphonomethylglycine.
(57) dimethylamine salt of N-phosphonomethylglycine.
(58) copper bis-(N-phosphonomethylglycine).
(59) zinc salt of N-(phosphonomethyl)glycine.
(60) N-phosphonomethylglycinamide.
(61) methyl-N-(phosphonomethyl)glycinate.
(62) ethyl-N-(phosphonomethyl)glycinate.
(63) n-propyl-N-(phosphonomethyl)glycinate.
(64) n-butyl-N-(phosphonomethyl)glycinate.
(65) cyclohexyl-N-(phosphonomethyl)glycinate.
(66) chloroethyl-N-(phosphonomethyl)glycinate.
(67) isopropylamine salt of N-phosphonomethylglycine.

(68) methylamine salt of N-phosphonomethylglycine.
(69) diisopropylamine salt of N-phosphonomethylglycine.
(70) pyridine salt of N-phosphonomethylglycine.
(71) aniline salt of N-phosphonomethylglycine.

Preferably, the above composition contains the compound of formula (I) and the compound (II) in a (I):(II) weight ratio of from 1:50 to 50:1, more preferably from 1:20 to 20:1, especially preferably from 1:10 to 10:1.

The amount of the composition to be actually applied varies depending upon many factors, for example the type of a plant whose growth is to be controlled. Suitably, it is generally 0.1 to 10 kg/ha, preferably 0.5 to 5 kg/ha. Any one skilled in the art can easily determine suitable proportions and amounts of the composition by an ordinary standardized test without conducting many experiments.

The composition of this invention may be applied in the form of a composition comprising the active ingredient and a carrier composed of a solid or liquid diluent. The composition may also include an additive such as a surface-active agent.

Examples of such diluents, carriers and surface-active agents may be those which have been cited hereinabove.

The composition of this invention can be used as a usual formulation, for example, as a solution, an emulsifiable concentrate, a suspension, a dust or a paste in combination with a carrier and/or a surface-active agent.

The composition of this invention can be prepared, for example, by mixing the compound (I) and the compound (II) and then with a carrier or other additives, and formulating the resulting mixture, or by separately preparing a composition comprising the compound (I) and a composition comprising the compound (II), adding a carrier or the like as required, and mixing the compositions, and formulating the mixture.

According to this invention, there is also provided a method of eradicating weeds, which comprises applying the compound of formula (I) and the compound of formula (II), simultaneously or successively, to a locus where weeds are growing in an amount effective for eradicating the weeds.

The compounds of formulae (I) and (II) may be applied simultaneously to the aforesaid locus as the composition comprising the two compounds, or as the composition of the compound (I) and the composition of the compound (II) separately prepared.

Alternatively, the composition of the compound (I) and the composition of the compound (II), separately prepared, may be applied to the aforesaid locus successively.

The sequence of applying the composition of the compound (I) and the composition of the compound (II) is not limited.

After one of the compositions is applied, the other may preferably be applied while the active compound (I) or (II) in the still remains on the foliage of the weeds. Usually, after one of the compositions is applied, the other may preferably be applied immediately or within 2 to 3 days, although this period may vary depending upon the type of the plant to be controlled, the climatic conditions, etc.

According to this invention, the compounds (I) and (II), for example, may be applied to a locus where a crop is cultivated before emergence of the crop. As a result, weeds growing in the locus before emergence of the crop can be killed.

The amount of the composition to be applied, as described above, is a suitable measure of the amounts of the compounds (I) and (II) used in the above method.

Advantageously, according to the above method of this invention, both broad-leaved weeds and narrow-leaved weeds can be eradicated by applying the above compounds in relatively low dosages.

According to the method of this invention, the following gramineous weeds can also be eradicated in addition to the broad-leaved weeds already exemplified hereinabove.

Gramineae
*Sorgum helepense,*
*Avena fatua,*
*Digitaria adsendens,*
*Setaria faberi,*
*Agropyron repens,*
*Panicum texanum,*
*Echinochloa crus-galli,*
*Setaria viridis,*
*Poa annua,*
*Eleusine indicate,*
*Axonopus affinis,*
*Bachiaria platyphylla,*
*Bromus tectorum,*
*Cynodon dactylon,*
*Panicum dichlotomiflorum,*
*Paspalum dilatatum,*
*Echinocloa colona,*
*Panicum capillare,*
*Setaria faberi,* and
*Alopecurus acqualis* var. amurensis.

The following weeds can also be the object of eradication in accordance with this invention.

Cyperaceae
*Cyperus rotundus,*
*Cyperus microiria,*
*Cyperus serotinus,*
*Scirpus hotarui,* and
*Eleocharis acicularis* var. longiseta.

Alismtaceae
*Sagittaria pygmaea.*

Pontederiacease
*Monochoria vaginalis.*

Thirdly, the present invention provides a herbicidal composition comprising as a herbicidal ingredient a combination of herbicidally effective amounts of the compound of formula (I) and a compound represented by the following formula (III)

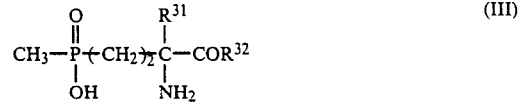

wherein $R^{31}$ represents a hydrogen atom or an alkyl group having 1 to 4 carbon atoms, and
$R^{32}$ represents —OH, —NH$_2$, —NHNH$_2$, —NHC$_6$H$_5$, or an alkoxy group having 1 to 12 carbon atoms which may be substituted by —OH, or an acid addition salt thereof or a salt thereof with a base, and a carrier and/or a surfactant.

In formula (III) above, $R^{31}$ represents a hydrogen atom or an alkyl group having 1 to 4 carbon atoms, $R^{32}$ represents —OH, —NH$_2$, —NHNH$_2$, —NHC$_6$H$_5$, or an alkoxy group having 1 to 12 carbon atoms which may be substituted by —OH.

Examples of the alkyl group for $R^{31}$ may be alkyl groups having 1 to 4 carbon atoms among the alkyl groups exemplified for X and Y in formula (I).

The alkoxy group for $R^{32}$ may be linear or branched, and includes, for example, methoxy, ethoxy, n-propoxy, iso-propoxy, n-butoxy, sec-butoxy, iso-butoxy, tert-butoxy, n-pentoxy, n-hexoxy, n-heptoxy, n-octoxy, n-nonanoxy, n-decanoxy, n-undecanoxy and dodecanoxy groups. These alkoxy groups may be substituted by a hydroxyl group (—OH). Thus, for example $R^{32}$ may represent a hydroxyethoxy group.

Compounds represented by formula (III) are disclosed in the above-cited U.S. Pat. No. 4,168,963, and believed to be known.

The compound of formula (III) may be used in the composition of this invention as an acid addition salt or a salt with a base.

Examples of acids for forming the acid addition salt may be those exemplified hereinabove with regard to the acid addition salts of the compounds of formula (II). It is believed that the acid addition salts are formed at the primary amino group in formula (III).

Examples of the base for forming the salt may be those exemplified above with regard to the compounds of formula (II).

In formula (III), $R^{31}$ is preferably a hydrogen atom and $R^{32}$ is preferably —OH, —NH$_2$, —NHNH$_2$, an alkoxy group having 1 to 4 carbon atoms, and a hydroxyalkoxy group having 2 to 4 carbon atoms.

Examples of preferred salts of the compounds of formula (III) include salts with Na, K, Cu, Mg, Ca, Zn, Ni, Mn and Fe, ammonium salts, salts with bases such as mono-, di- or tri-alkylamines having 1 to 4 carbon atoms in each alkyl moiety, or aniline, acid addition salts with acids such as hydrochloric acid, sulfuric acid, hydrobromic acid, chloric acid or oxalic acid.

The salts of the compounds of formula (III) with the acids or bases may be produced by known methods from the compounds of formula (III) and the acids or bases.

Examples of the compounds of formula (II) and their acid addition salts or their salts with bases which are preferably used in this invention are shown below.

(100) [(3-amino-3-carboxy)-propyl-1]-methyl-phosphinic acid
(101) [(3-amino-3-carboxy)-propyl-1]-methyl-phosphinic acid monosodium salt
(102) [(3-amino-3-carboxy)-propyl-1]-methyl-phosphinic acid monopotassium salt
(103) [(3-amino-3-carboxy)-propyl-1]-methyl-phosphinic acid monoammonium salt
(104) [(3-amino-3-carboxy)-propyl-1]-methyl-phosphinic acid diammonium salt
(105) [(3-amino-3-carboxy)-propyl-1]-methyl-phosphinic acid magnesium salt
(106) [(3-amino-3-carboxy)-propyl-1]-methyl-phosphinic acid monopropylammonium salt
(107) [(3-amino-3-carboxy)-propyl-1]-methyl-phosphinic acid mono(diisopropylammonium) salt
(108) [(3-amino-3-carbomethoxy)-propyl-1]-methyl-phosphinic acid
(109) [(3-amino-3-carbomethoxy)-propyl-1]-methyl-phosphinic acid sodium salt
(110) [(3-amino-3-carbomethoxy)-propyl-1]-methyl-phosphinic acid diisopropylammonium salt
(111) [(3-amino-3-carbamido)-propyl-1]methylphosphinic acid
(112) [(3-amino-3-carbamido)-propyl-1]-methylphosphinic acid sodium salt
(113) [(3-amino-3-carbamido)-propyl-1]-methylphosphinic acid ammonium salt
(114) [(3-amino-3-carboxy)-propyl-1]-methylphosphinic acid
(115) [(3-amino-3-carboxy)-propyl-1]-methylphosphinic acid monosodium salt
(116) [(3-amino-3-carboxy)-propyl-1]-methylphosphinic acid monoammonium salt Preferably, the above composition contains the compound of formula (I) and the compound (III) in a (I):(III) weight ratio of from 1:50 50:1, more preferably from 1:20 to 20:1, especially preferably from 1:10 to 10:1.

The amount of the composition to be actually applied varies depending upon many factors, for example the type of a plant whose growth is to be controlled. Suitably, it is generally 0.1 to 10 kg/ha, preferably 0.5 to 5 kg/ha. Any one skilled in the art can easily determine the suitable proportions and amounts of the composition by an ordinary standardized test without conducting many experiments.

The composition of this invention may be applied in the form of a composition comprising the active ingredient and a carrier composed of a solid or liquid diluent. The composition may also include an additive such as a surface-active agent.

Examples of such diluents, carriers and surface-active agents may be those which have been cited hereinabove.

The composition of this invention can be used as a usual formulation, for example, as a solution, an emulsifiable concentrate, a suspension, a dust or a paste in combination with a carrier and/or a surface-active agent.

The composition of this invention can be prepared, for example, by mixing the compound (I) and the compound (III) and then with a carrier or other additives, and formulating the resulting mixture, or by separately preparing a composition comprising the compound (I) and a composition comprising the compound (III), adding a carrier or the like as required, and mixing the compositions, and formulating the mixture.

According to this invention, there is also provided a method of eradicating weeds, which comprises applying the compound of formula (I) and the compound of formula (III), simultaneously or successively, to a locus where weeds are growing in an amount effective for eradicating the weeds.

The compounds of formulae (I) and (III) may be applied simultaneously to the aforesaid locus as the composition comprising the two compounds, or as the composition of the compound (I) and the composition of the compound (III) separately prepared.

Alternatively, the composition of the compound (I) and the composition of the compound (III), separately prepared, may be applied to the aforesaid locus successively.

The sequence of applying the composition of the compound (I) and the composition of the compound (III) is not limited.

After one of the compositions is applied, the other may preferably be applied while the active compound (I) or (III) in the still remains on the foliage of the weeds. Usually, after one of the compositions is applied, the other may preferably be applied immediately or within 2 to 3 days, although this period may vary depending upon the type of the plant to be controlled, the climatic conditions, etc.

According to this invention, the compounds (I) and (III), for example, may be applied to a locus where a crop is cultivated before emergence of the crop. As a result, weeds growing in the locus before emergence of the crop can be killed.

The amount of the composition to be applied, as described above, is a suitable measure of the amounts of the compounds (I) and (III) used in the above method.

Advantageously, according to the above method of this invention, both broad-leaved weeds and narrow-leaved weeds can be eradicated by applying the above compounds in relatively low dosages.

According to the method of this invention, the following gramineous weeds can also be eradicated in addition to the broad-leaved weeds already exemplified hereinabove.

Gramineae
*Sorgum helepense,*
*Digitaria adsendens,*
*Setaria faberi,*
*Panicum texanum,*
*Echinochloa crus-galli,*
*Setaria viridis,*
*Poa annua,*
*Eleusine indicate,*
*Axonopus affinis,*
*Bachiaria platyphylla,*
*Bromus tectorum,*
*Panicum dichotomiflorum,*
*Paspalum dilatatum,*
*Echinocloa colona,*
*Panicum capillare,*
*Setaria faberi,* and
*Alopecurus acqualis* var. amurensis.

The following weeds can also be the object of eradication in accordance with this invention.

Cyperaceae
*Cyperus microiria,*
*Scirpus hotarui,* and
*Eleocharis acicularis* var. longiseta.
Alismtaceae
*Sagittaria pygmaea.*
Pontederiacease
*Monochoria vaginalis*

The following examples illustrate the present invention in greater detial.

In these examples, all parts are by weight unless otherwise specified. The herbicidal activity of the active test compounds was evaluated on a scale of 0 to 5 in which 0 means that the plants were as sound as before the application of the active compound and 5 means that the application of the active compound caused the plants to wither and die, and 1, 2, 3 and 4 mean varying degrees of the enfeebled state of the plants between 0 and 5.

PRODUCTION EXAMPLES

EXAMPLE 1

Synthesis of methyl 2-hydroxy-4-(2-chloro-4-trifluoromethylphenoxy)benzoate:

A mixture of 45.5 parts of 85% KOH, 250 parts by volume of methanol and 13 parts of water was added to a solution of 50.8 parts of 2,4-dihydroxybenzoic acid in 300 parts by weight of methanol. The mixture was stirred at room temperature for 30 minutes, and then concentrated to dryness under reduced pressure. To the residue were added 71 parts of 3,4-dichlorobenzotrifluoride and 250 parts by volume of dimethyl sulfoxide, and the mixture was heated with stirring at 150° to 160° C. for about 20 hours. After cooling, water was added, and the unreacted matter was extracted by using ether. The aqueous layer was acidified with HCl, and the precipitated crystals were collected by filtration.

Methanol (400 parts by volume) and 0.1 part by volume of concentrated sulfuric acid were added to 20 parts of the crystals, and the mixture was refluxed. About 10 hours later, methanol was removed by concentration under reduced pressure. Ethyl acetate was added to the residue, and the solution was washed twice with 1N aqeuous NaOH solution. The organic layer was washed with water and dried over anhydrous sodium sulfate. The organic solvent was removed under reduced pressure to give 18 parts of the captioned compound.

EXAMPLE 2

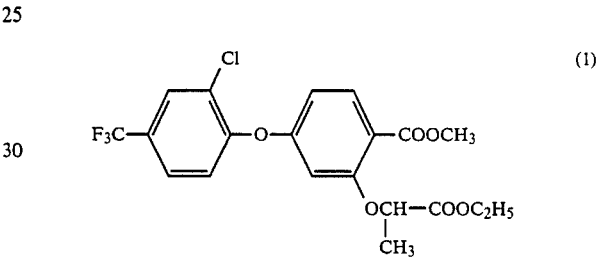

Ethyl alpha-bromopropionate (0.89 part), 1.36 parts of anhydrous potassium carbonate and 40 parts by volume of methyl ethyl ketone were added to 1.7 parts of methyl 2-hydroxy-4-(2-chloro-4-trifluoromethylphenoxy)-benoate synthesized in Example 1, and the mixture was refluxed for about 6 hours.

After cooling, water was added, and the organic layer was extracted and separated, washed with 1N aqueous NaOH solution and further with water, and dried over anhydrous sodium sulfate. The solvent was removed under reduced pressure to give 1.9 parts of the captioned compound (1). The IR and NMR spectral data of the compound are shown in Table 1.

EXAMPLE 3

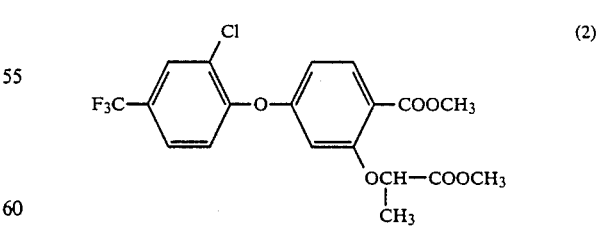

Example 2 was repeated except that 0.6 part of methyl alpha-chloropropionate was used instead of ethyl alpha-bromopropionate, and the refluxing was carried out for about 10 hours. There was obtained 0.9 part of the captioned compound. The IR and NMR spectral data of this compound are shown in Table 1.

EXAMPLE 4

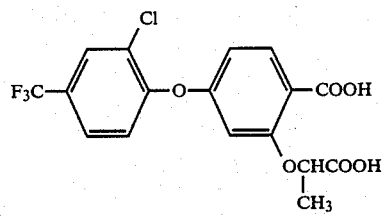
(4)

Ethanol (4 parts by volume), 1.5 parts by volume of water and 17 parts by volume of 1N aqueous KOH solution were added to 1.9 parts of the compound (1) synthesized in Example 2, and the mixture was stirred for one day at room temperature. The reaction mixture was concentrated, and water was added. The mixture was acidified with HCl and extracted with ether. The layer was dried over anhydrous sodium sulfate, and the solvent was removed under reduced pressure to give 1.2 parts of the captioned compound (4). The IR and NMR spectral data of this compound are shown in Table 1.

EXAMPLE 5

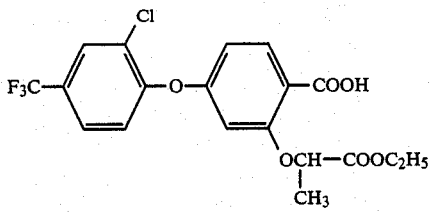
(3)

Thionyl chloride (2.26 parts) was added to 1.92 parts of 2-[2-carboxy-5-(2-chloro-4-trifluoromethylphenoxy)]phenoxypropionic acid (4) synthesized in Example 4, and the mixture was heated with stirring at 60° to 70° C. for about 3 hours. The excess of thionyl chloride was removed under reduced pressure. The residue was dissolved in 6 parts by volume of benzene, and a mixture of 0.22 part of ethanol, 0.53 part of triethylamine and 10 parts by volume of benzene was added dropwise to this solution under ice cooling over about 20 minutes. After the addition, the mixture was stirred at room temperature for about 1 hour, and then water was added. The solution was then extracted with benzene, and the organic layer was washed with water, and dried over anhydrous sodium sulfate. The solvent was removed under reduce pressure to obtain a crude product. The crude product was purified by silica gel chromatography to give 0.5 part of the captioned compound (3). The IR and NMR spectral data of this compound are shown in Table 1.

EXAMPLE 6

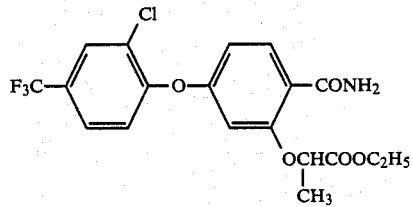
(6)

Thionyl chloride (0.8 part by volume) was added to 0.1 part of the compound (3) synthesized in Example 5, and the mixture was heated at 70° C. with stirring for about 3 hours. The excess of thionyl chloride was removed under reduced pressure, and the residue was dissolved in 2 parts by volume of benzene. Liquid ammonia was blown into the solution under ice cooling. The resulting precipitate was separated by filtration. Water was added to the filtrate and the solution was extracted with benzene. The organic layer was washed with water and dried over anhydrous sodium sulfate. The solvent was removed under reduced pressure to give 0.1 part of the captioned compound (6). The IR and NMR spectral data of this compound are shown in Table 1.

EXAMPLE 7

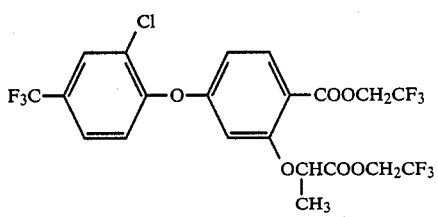
(7)

Thionyl chloride (3 parts by weight) was added to 3 parts of the compound (4) synthesized in Example 4, and the mixture was heated with stirring at 60° to 70° C. for 3 hours. The excess of thionyl chloride was removed under reduced pressure, and the residue was dissolved in 6 parts by volume of benzene. A mixture of 1.9 parts of 2,2,2-trifluoroethanol, 1.7 parts of triethylamine and 6 parts by volume of benzene was added dropwise to the solution under ice cooling. The mixture was stirred at room temperature for 3 hours, and then water was added. The mixture was extracted with benzene. The organic layer was washed with a saturated aqueous solution of sodium bicarbonate and then with water, and dried over anhydrous sodium sulfate. The solvent was removed under reduced pressure to give 3.3 parts of the captioned compound (7). The IR and NMR spectral data of this compound are shown in Table 1.

EXAMPLE 8

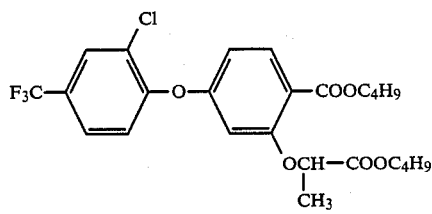
(5)

Example 7 was repeated except that 1.4 parts of n-butyl alcohol was used instead of 2,2,2-trifluoroethanol. There was used 2.9 parts of the captioned compound (5). The IR and NMR spectral data of this compound are shown in Table 1.

EXAMPLE 9

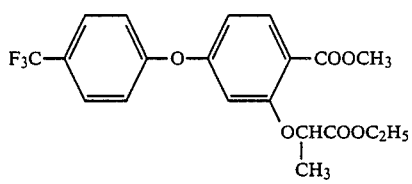

Example 2 was repeated except that 1.5 parts of methyl 2-hydroxy-4-(4-trifluoromethylphenoxy)benzoate was used instead of methyl 2-hydroxy-4-(2-chloro-4-trifluoromethylphenoxy)benzoate. There was obtained 0.9 part of the captioned compound (8). The IR and NMR spectral data of this compound are shown in Table 1.

EXAMPLE 10

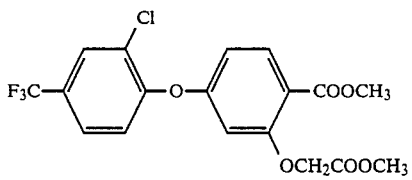

Example 2 was repeated except that 0.75 part of methyl alpha-bromoacetate was used instead of ethyl alpha-bromopropionate. The captioned compound was obtained in an amount of 1.8 parts. The IR and NMR spectral data of this compound are shown in Table 1.

EXAMPLE 11

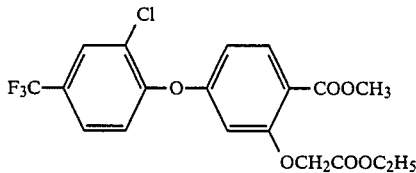

Example 2 was repeated except that 0.81 part of ethyl alpha-bromoacetate was used instead of ethyl alpha-bromopropionate. There was obtained 1.9 parts of the captioned compound (10). The IR and NMR spectral data of this compound are shown in Table 1.

EXAMPLE 12

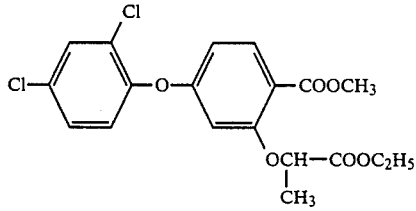

Example 2 was repeated except that 1.53 parts of methyl 2-hydroxy-4-(2,4-dichlorophenoxy)benzoate was used instead of methyl 2-hydroxy-4-(2-chloro-4-trifluoromethylphenoxy)benzoate. There was obtained 1.7 parts of the captioned compound (12). The IR and NMR spectral data of this compound are shown in Table 1.

EXAMPLE 13

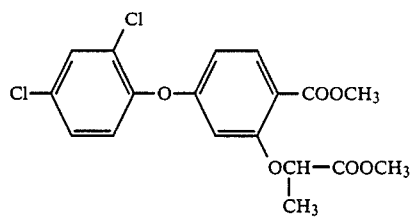

Example 12 was repeated except that 0.82 part of methyl alpha-bromopropionate was used instead of ethyl alpha-bromopropionate. There was obtained 1.7 parts of the captioned compound (11). The IR and NMR spectral data of this compound are shown in Table 1.

EXAMPLE 14

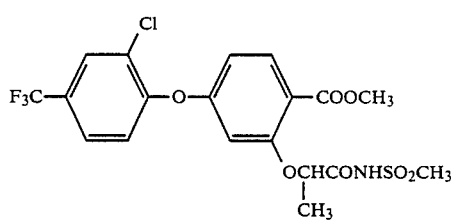

To 1.7 parts of methyl 2-hydroxy-4-(2-chloro-4-trifluoromethylphenoxy)benzoate synthesized in Example 1 were added 1.13 parts of N-(alpha-bromopropionyl)-methanesulfonamide, 1.4 parts of anhydrous potassium carbonate and 40 parts by volume of dimethyl sulfoxide, and the mixture was reacted at 100° C. for about 5 hours. After cooling, water was added to the reaction mixture, and the mixture was acidified with dilute hydrochloric acid and then extracted with ether. The organic layer was dried over anhydrous sodium sulfate, and the solvent was removed under reduced pressure to give 2.1 parts of the captioned compound (13). The IR and NMR spectral data of this compound are shown in Table 1.

EXAMPLE 15

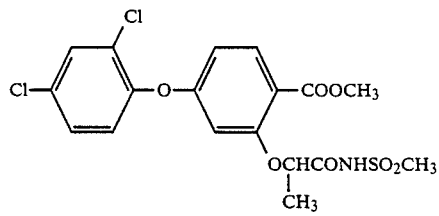

Example 14 was repeated except that 1.53 parts of methyl 2-hydroxy-4-(2,4-dichlorophenoxy)benzoate was used instead of methyl 2-hydroxy-4-(2-chloro-4-trifluoromethylphenoxy)benzoate, and the reaction was carried out at 100° C. for about 3 hours. There was obtained 2.1 parts of the captioned compound (13). The IR and NMR spectral data of this compound are shown in Table 1.

EXAMPLE 16

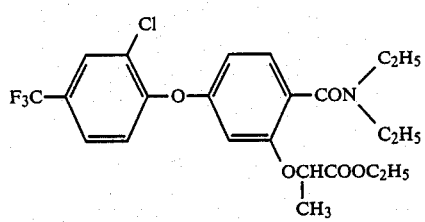

Example 6 was repeated except that an ether solution of diethylamine was added instead of liquid ammonia. There was obtained 0.1 part of the captioned compound (16). The IR and NMR spectral data of this compound are shown in Table 1.

EXAMPLE 17

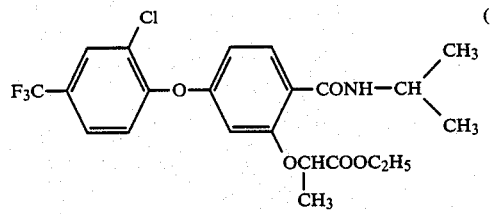

Example 6 was repeated except that an ether solution of isopropylamine was added instead of liquid ammonia. There was obtained 0.1 part of the captioned compound (15). The IR and NMR spectral data of this compound are shown in Table 1.

EXAMPLE 18

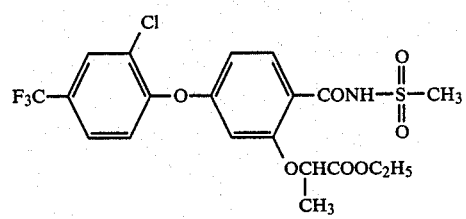

Example 6 was repeated except that methanesulfonamide was added instead of liquid ammonia. There was obtained 0.08 part of the captioned compound (14). The IR and NMR spectral data of this compound are shown in Table 1.

EXAMPLE 19

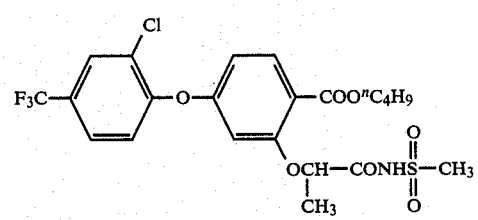

Example 14 was repeated except that n-butyl 2-hydroxy-4-(2-chloro-4-trifluoromethylphenoxy)benzoate was used instead of methyl 2-hydroxy-4-(2-chloro-4-trifluoromethylphenoxy)benzoate. There was used 1.9 parts of the captioned compound (18). The IR and NMR spectral data of this compound are shown in Table 1.

EXAMPLE 20

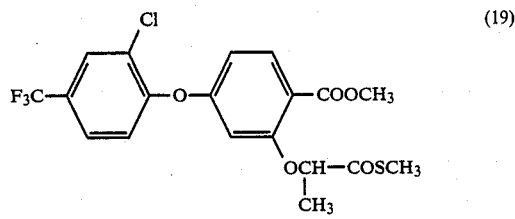

S-methyl 2-bromopropanethioate (2.9 parts), by volume of methyl ethyl ketone were added to 1.73 parts of methyl 2-hydroxy-4-(2-chloro-4-trifluoromethylphenoxy)benzoate synthesized in Example 1. The mixture was stirred at 60° C. for about 8 hours. After cooling, water was added to the reaction mixture. The organic layer was extracted, washed with a saturated aqueous solution of sodium bicarbonate and further with water, and dried over anhydrous sodium sulfate. The solvent was removed under reduced pressure. The crude product was purified by silica gel column chromatography to give 0.6 part of the captioned compound (19). The IR and NMR spectral data of the resulting compound are shown in Table 1.

EXAMPLE 21

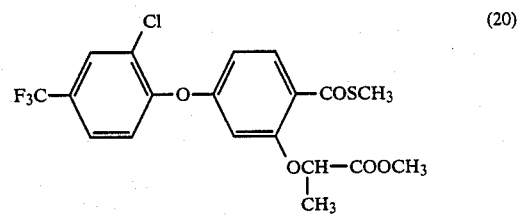

Thionyl chloride (0.26 part by volume) was added to 0.5 part of methyl 2-[2-carboxy-5-(2-chloro-4-trifluoromethylphenoxy)]phenoxypropionate, and the mixture was stirred at 70° C. for about 2 hours. The excess of thionyl chloride was removed under reduced pressure, and the residue was dissolved in 3 parts by volume of benzene. The solution was added to a mixture of 0.56 part of a 15% aqueous solution of methylmercaptan sodium salt and 3 parts by volume of benzene under cooling (8° to 10° C.) with stirring. The mixture was stirred at room temperature for about 2 hours. The organic layer was then separated, washed with water, and dried over anhydrous sodium sulfate. The solvent was removed under reduced pressure.

The crude product was purified by silica gel chromatography to give 0.2 part of the captioned compound (20). The IR and NMR spectral data of the compound are shown in Table 1.

EXAMPLE 22

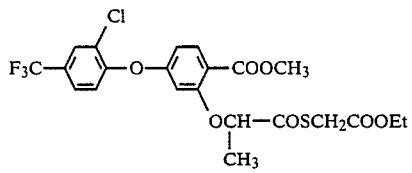
(21)

Thionyl chloride (0.3 part by volume) was added to 0.5 part of S-ethoxycarbonylmethyl 2-[2-carboxy-5-(2-chloro-4-trifluoromethylphenoxy)]phenoxypropanethioate, and the mixture was stirred at 70° C. for 2 hours. The excess of thionyl chloride was removed under reduced pressure, and the residue was dissolved in 3 parts by volume of benzene. The solution was added to 0.035 part of methanol and a solution of 0.11 part of triethylamine in 15 parts by volume of benzene under cooling (8° to 15° C.) with stirring. After the addition, the mixture was stirred at room temperature for about 2 hours. The organic layer was then separated, washed with water, and dried over anhydrous sodium sulfate. The solvent was removed under reduced pressure. The resulting crude product was purified by silica gel chromatography to give 0.4 part of the captioned compound (21). The IR and NMR spectral data of the compound are shown in Table 1.

EXAMPLE 23

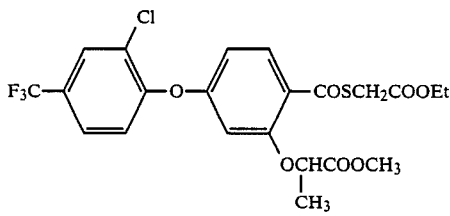
(22)

The captioned compound (22) (0.5 part) was obtained by operating in the same way as in Example 21 except that 0.14 part of ethyl thioglycolate and 0.13 part of triethylamine were used instead of the methylmercaptan sodium salt (15% aqueous solution). The IR and NMR spectral data of the compound are shown in Table 1.

EXAMPLE 24

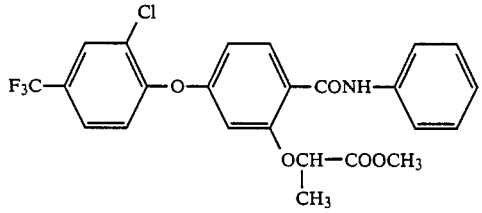
(23)

Thionyl chloride (0.3 part by volume) was added to 0.5 part of methyl 2-[2-carboxy-5-(2-chloro-4-trifluoromethylphenoxy)]phenoxypropionate, and the mixture was stirred at 60° C. for 3 hours. The excess of thionyl chloride was removed under reduced pressure, and the residue was dissolved in 3 parts by volume of ether. The solution was added with stirring to a solution of 0.13 part of aniline and 0.14 part of triethylamine in 15 parts by volume of ether under cooling (about 10° C.). After the addition, the mixture was stirred at room temperature for about 2 hours. The organic layer was then separated, washed with water, and dried over anhydrous sodium sulfate. The solvent was then removed under reduced pressure. The crude product was purified by silica gel column chromatography to give 0.74 part of the captioned compound (23). The IR and NMR spectral data are shown in Table 1.

EXAMPLE 25

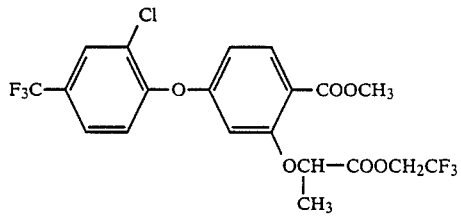
(24)

The captioned compound (24) (0.35 part) was prepared in the same way as in Example 22 except that 0.48 part of 2',2',2'-trifluoroethyl 2-[2-carboxy-5-(2-chloro-4-trifluoromethylphenoxy)]phenoxypropionate was used instead of the S-ethoxycarbonylmethyl 2-[2-carboxy-5-(2-chloro-4-trifluoromethylphenoxy)]phenoxypropanethioate. The IR and NMR spectral data of the compound are shown in Table 1.

EXAMPLE 26

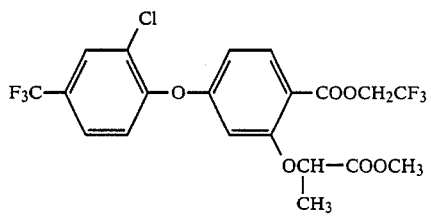
(25)

The captioned compound (25) (0.4 part) was obtained in the same way as in Example 24 except that 2,2,2-trifluoroethanol was used instead of aniline. The IR and NMR spectral data of the compound are shown in Table 1.

EXAMPLE 27

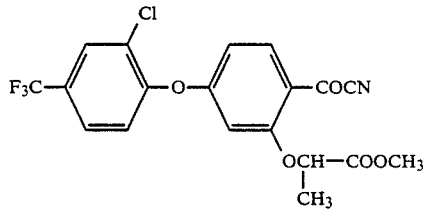
(26)

Thionyl chloride (0.4 part by volume) was added to 0.87 part of methyl 2-[2-carboxy-5-(2-chloro-4-trifluoromethylphenoxy)propionate, and the mixture was stirred at 70° C. for 2 hours. The excess of thionyl chloride was removed under reduced pressure, and 0.62 part of tri-n-butyltin cyanide was added to the residue. The mixture was stirred at 70° C. for 20 minutes. After the reaction, the reaction mixture was purified by silica gel column chromatography to give 0.15 part of the captioned compound (26). The IR and NMR spectral data of the compound are shown in Table 1.

EXAMPLE 28

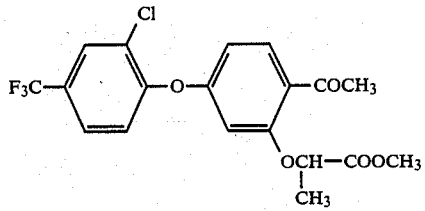
(27)

Methyl alpha-bromopropionate (5.7 parts), 9.4 parts of anhydrous potassium carbonate and 350 parts by volume of methyl ethyl ketone were added to 10.2 parts of 2'-hydroxy-4'-(2-chloro-4-trifluoromethylphenoxy)acetophenone (synthesized in the same way as in Example 1 except that 2',4'-dihydroxyacetophenone was used instead of 2,4-dihydroxybenzoic acid. The mixture was refluxed for about 6 hours. After cooling, water was added, and the organic layer was extracted. The separated organic layer was washed with 1N-NaOH and then with water, and dried over anhydrous sodium sulfate. The solvent was removed under reduced pressure to give 11.5 parts of the captioned compound (27). The IR and NMR spectral data of the compound are shown in Table 1.

EXAMPLE 29

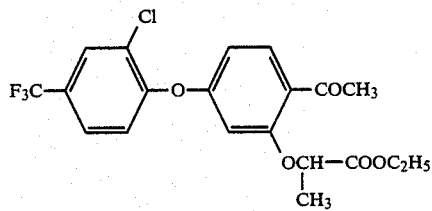
(28)

The captioned compound (28) (11.8 parts) was obtained in the same way as in Example 28 except that 6.2 parts of ethyl alpha-bromopropionate was used instead of methyl alpha-bromopropionate. The IR and NMR spectral data of the compound are shown in Table 1.

EXAMPLE 30

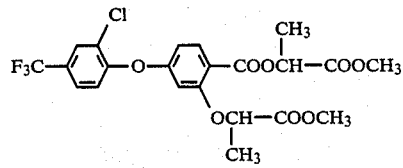
(29)

A mixture of 2.0 parts of 2-hydroxy-4-(2-chloro-4-trifluoromethylphenoxy)benzoic acid, 1.0 part of methyl alpha-bromopropionate, 2.5 parts of anhydrous potassium carbonate and 30 parts by volume of methyl ethyl ketone was refluxed for 2 hours. After the reaction, water was added, and the organic layer was separated, washed twice with 1N-NaOH and further with water, and dried over anhydrous sodium sulfate. The organic solvent was removed under reduced pressure. The crude product was purified by silica gel column chromatography to give 0.8 part of the captioned compound (29). The IR and NMR spectra data of the compound are shown in Table 1.

EXAMPLE 31

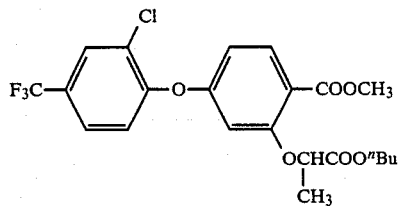
(30)

The captioned compound (30) (0.3 part) was prepared in the same way as in Example 22 except that 0.46 part of n-butyl 2-[2-carboxy-5-(2-chloro-4-trifluoromethylphenoxy)]phenoxypropionate was used instead of S-ethoxycarbonylmethyl 2-[2-carboxy-5-(2-chloro-4-trifluoromethylphenoxy)]phenoxypropanethioate. The IR and NMR spectral data of the compound are shown in Table 1.

EXAMPLE 32

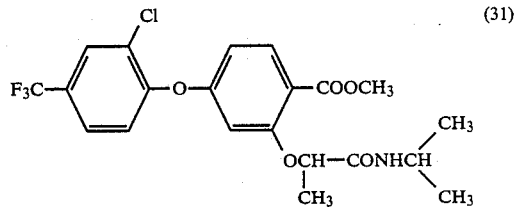
(31)

The captioned compound (31) was prepared in the same way as in Example 22 except that 0.44 part of N-isopropyl-2-[2-methoxycarbonyl-5-(2-chloro-4-trifluoromethylphenoxy)]phenoxypropionamide was used instead of S-ethoxycarbonylmethyl 2-[2-carboxy-5-(2-chloro-4-trifluoromethylphenoxy)]phenoxypropanethioate. The IR and NMR spectral data are shown in Table 1.

TABLE 1

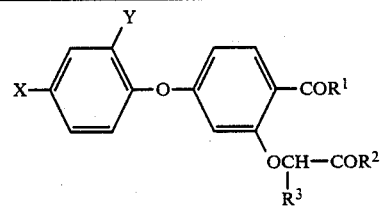

| Example No. | Compound No. | X | Y | $R^1$ | $R^2$ | $R^3$ | IR $\nu(cm^{-1})$ | NMR $^{in}CDCl_3$ $\delta(ppm)$ |
|---|---|---|---|---|---|---|---|---|
| 2 | (10 | $CF_3$ | Cl | $OCH_3$ | $OC_2H_5$ | $CH_3$ | 1755 | 1.20 (3H) |

TABLE 1-continued

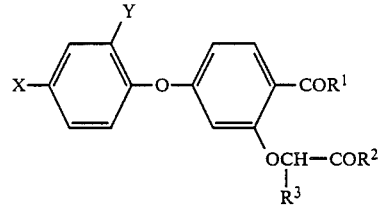

| Example No. | Compound No. | X | Y | R¹ | R² | R³ | IR $\nu$(cm$^{-1}$) | NMR in CDCl$_3$ $\delta$(ppm) | |
|---|---|---|---|---|---|---|---|---|---|
| | | | | | | | 1730 | 1.63 | (3H) |
| | | | | | | | 1595 | 3.86 | (3H) |
| | | | | | | | 1490 | 4.15 | (2H) |
| | | | | | | | 1320 | 4.68 | (1H) |
| | | | | | | | 1125 | 6.47–6.63 | (2H) |
| | | | | | | | | 7.07 | (1H) |
| | | | | | | | | 7.50 | (1H) |
| | | | | | | | | 7.70–7.90 | (2H) |
| 3 | (2) | CF$_3$ | Cl | OCH$_3$ | OCH$_3$ | CH$_3$ | 1750 | 1.67 | (3H) |
| | | | | | | | 1730 | 3.70 | (3H) |
| | | | | | | | 1595 | 3.86 | (3H) |
| | | | | | | | 1490 | 4.71 | (1H) |
| | | | | | | | 1320 | 6.47–6.63 | (2H) |
| | | | | | | | 1125 | 7.07 | (1H) |
| | | | | | | | | 7.50 | (1H) |
| | | | | | | | | 7.70–7.90 | (2H) |
| 4 | (4) | CF$_3$ | Cl | OH | OH | CH$_3$ | 2600–3400 (broad) | 1.71 | (3H) |
| | | | | | | | | 4.95 | (1H) |
| | | | | | | | | 6.40–6.67 | (2H) |
| | | | | | | | 1700–1730 (broad) | 7.17 | (1H) |
| | | | | | | | | 7.57 | (1H) |
| | | | | | | | | 7.73 | (1H) |
| | | | | | | | 1590 | 7.96 | (1H) |
| | | | | | | | | 10.40 | (2H) |
| 5 | (3) | CF$_3$ | Cl | OH | OC$_2$H$_5$ | CH$_3$ | 3300 | 1.27 | (3H) |
| | | | | | | | 1750 | 1.73 | (3H) |
| | | | | | | | 1720 | 4.27 | (2H) |
| | | | | | | | 1595 | 4.27 | (2H) |
| | | | | | | | 1490 | 6.50–6.67 | (2H) |
| | | | | | | | 1320 | 7.17 | (1H) |
| | | | | | | | 1130 | 7.60 | (1H) |
| | | | | | | | | 7.76 | (1H) |
| | | | | | | | | 8.10 | (1H) |
| | | | | | | | | 8.63 | (1H) |
| 6 | (6) | CF$_3$ | Cl | NH$_2$ | OC$_2$H$_5$ | CH$_3$ | 3450 | 1.27 | (3H) |
| | | | | | | | 3200 | 1.68 | (3H) |
| | | | | | | | 1740 | 4.23 | (2H) |
| | | | | | | | 1660 | 4.92 | (1H) |
| | | | | | | | 1590 | 6.23–6.77 | (4H) |
| | | | | | | | 1490 | 7.07 | (1H) |
| | | | | | | | 1320 | 7.53 | (1H) |
| | | | | | | | 1125 | 7.75 | (1H) |
| | | | | | | | | 8.17 | (1H) |
| 7 | (7) | CF$_3$ | Cl | OCH$_2$CF$_3$ | OCH$_2$CF$_3$ | CH$_3$ | 1775 | 1.70 | (3H) |
| | | | | | | | 1740 | 4.30–4.84 | (4H) |
| | | | | | | | 1600 | 4.85 | (1H) |
| | | | | | | | 1490 | 6.48–6.63 | (2H) |
| | | | | | | | 1320 | 7.11 | (1H) |
| | | | | | | | 1130 | 7.55 | (1H) |
| | | | | | | | | 7.76 | (1H) |
| | | | | | | | | 7.92 | (1H) |
| 8 | (5) | CF$_3$ | Cl | OC$_4$H$_9$ | OC$_4$H$_9$ | CH$_3$ | 1750 | 0.87–1.70 | (17H) |
| | | | | | | | 1720 | 4.05–4.33 | (4H) |
| | | | | | | | 1600 | 4.70 | (1H) |
| | | | | | | | 1490 | 6.40–6.80 | (2H) |
| | | | | | | | 1320 | 7.07–7.73 | (4H) |
| | | | | | | | 1130 | | |
| 9 | (8) | CF$_3$ | H | OCH$_3$ | OC$_2$H$_5$ | CH$_3$ | 1755 | 1.23 | (3H) |
| | | | | | | | 1730 | 1.60 | (3H) |
| | | | | | | | 1595 | 3.86 | (3H) |
| | | | | | | | 1490 | 4.20 | (2H) |
| | | | | | | | 1320 | 4.76 | (1H) |
| | | | | | | | 1125 | 6.23–6.50 | (5H) |
| | | | | | | | | 7.60–7.76 | (2H) |
| 10 | (9) | CF$_3$ | Cl | OCH$_3$ | OCH$_3$ | H | 1760 | 3.76 | (3H) |
| | | | | | | | 1730 | 3.88 | (3H) |
| | | | | | | | 1595 | 4.68 | (2H) |
| | | | | | | | 1490 | 6.50–6.67 | (2H) |
| | | | | | | | 1320 | 7.10 | (1H) |

TABLE 1-continued
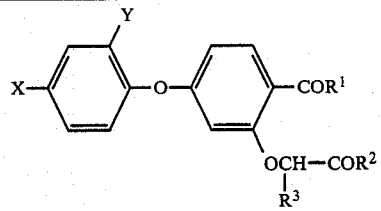
| Example No. | Compound No. | X | Y | R¹ | R² | R³ | IR $\nu(cm^{-1})$ | NMR in CDCl₃ $\delta$(ppm) | |
|---|---|---|---|---|---|---|---|---|---|
| | | | | | | | 1125 | 7.53 | (1H) |
| | | | | | | | | 7.73–7.95 | (2H) |
| 11 | (10) | CF₃ | Cl | OCH₃ | OC₂H₅ | H | 1755 | 1.27 | (3H) |
| | | | | | | | 1730 | 3.88 | (3H) |
| | | | | | | | 1595 | 4.25 | (2H) |
| | | | | | | | 1320 | 4.67 | (2H) |
| | | | | | | | 1250 | 6.50–6.67 | (2H) |
| | | | | | | | 1125 | 7.10 | (1H) |
| | | | | | | | | 7.53 | (1H) |
| | | | | | | | | 7.73–7.96 | (2H) |
| 12 | (11) | Cl | Cl | OCH₃ | OC₂H₅ | CH₃ | 1750 | 1.21 | (3H) |
| | | | | | | | 1730 | 1.65 | (3H) |
| | | | | | | | 1605 | 3.86 | (3H) |
| | | | | | | | 1575 | 4.17 | (2H) |
| | | | | | | | 1250 | 4.68 | (1H) |
| | | | | | | | 1130 | 6.43–6.60 | (2H) |
| | | | | | | | | 7.03–7.20 | (2H) |
| | | | | | | | | 7.40 | (1H) |
| | | | | | | | | 7.83 | (1H) |
| 13 | (11) | Cl | Cl | OCH₃ | OCH₃ | CH₃ | 1755 | 1.65 | (3H) |
| | | | | | | | 1730 | 3.70 | (3H) |
| | | | | | | | 1605 | 3.86 | (3H) |
| | | | | | | | 1575 | 4.70 | (1H) |
| | | | | | | | 1250 | 6.23–6.63 | (2H) |
| | | | | | | | 1130 | 7.03–7.20 | (2H) |
| | | | | | | | | 7.41 | (1H) |
| | | | | | | | | 7.83 | (1H) |
| 14 | (13) | CF₃ | Cl | OCH₃ | —NHSO₂CH₃ | CH₃ | 3300 | 1.70 | (3H) |
| | | | | | | | 1700 | 3.30 | (3H) |
| | | | | | | | 1600 | 3.95 | (3H) |
| | | | | | | | 1575 | 4.83 | (1H) |
| | | | | | | | 1255 | 6.53 | (1H) |
| | | | | | | | 1160 | 6.60 | (1H) |
| | | | | | | | | 7.0–7.8 | (3H) |
| | | | | | | | | 7.90 | (1H) |
| | | | | | | | | 11.0–11.7 | (1H) |
| 15 | (17) | Cl | Cl | OCH₃ | —NHSO₂CH₃ | CH₃ | 3300 | 1.70 | (3H) |
| | | | | | | | 1700 | 3.27 | (3H) |
| | | | | | | | 1605 | 3.90 | (3H) |
| | | | | | | | 1575 | 4.80 | (1H) |
| | | | | | | | 1245 | 6.40 | (1H) |
| | | | | | | | 1140 | 6.50 | (1H) |
| | | | | | | | | 7.0–7.5 | (3H) |
| | | | | | | | | 7.90 | (1H) |
| | | | | | | | | 11.3–11.7 | (1H) |
| 16 | (16) | CF₃ | Cl | N(C₂H₅)₂ | OC₂H₅ | CH₃ | 1750 | 0.96–1.33 | (9H) |
| | | | | | | | 1630 | 1.55 | (3H) |
| | | | | | | | 1595 | 3.10–3.83 | (4H) |
| | | | | | | | 1320 | 4.13 | (2H) |
| | | | | | | | 1260 | 4.63 | (1H) |
| | | | | | | | 1130 | 6.40 | (1H) |
| | | | | | | | | 6.55 | (1H) |
| | | | | | | | | 6.96 | (1H) |
| | | | | | | | | 7.13–7.53 | (2H) |
| | | | | | | | | 7.70 | (1H) |
| 17 | (15) | CF₃ | Cl | NHCH(CH₃)₂ | OC₂H₅ | CH₃ | 3400 | 1.13–1.40 | (9H) |
| | | | | | | | 1745 | 1.67 | (3H) |
| | | | | | | | 1645 | 4.03–4.47 | (3H) |
| | | | | | | | 1595 | 4.92 | (1H) |
| | | | | | | | 1320 | 6.50–6.67 | (2H) |
| | | | | | | | 1260 | 7.03 | (1H) |
| | | | | | | | 1125 | 7.50 | (1H) |
| | | | | | | | | 7.70 | (1H) |
| | | | | | | | | 7.83–8.20 | (2H) |
| 18 | (14) | CF₃ | Cl | NHSO₂CH₃ | OC₂H₅ | CH₃ | 3300 | 1.30 | (3H) |

TABLE 1-continued
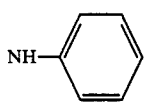
| Example No. | Compound No. | X | Y | R¹ | R² | R³ | IR ν(cm⁻¹) | NMR in CDCl₃ δ(ppm) | |
|---|---|---|---|---|---|---|---|---|---|
| | | | | | | | 1740 | 1.73 | (3H) |
| | | | | | | | 1680 | 3.40 | (3H) |
| | | | | | | | 1600 | 4.27 | (2H) |
| | | | | | | | 1260 | 5.00 | (1H) |
| | | | | | | | 1160 | 6.5–6.7 | (2H) |
| | | | | | | | | 7.1–7.8 | (3H) |
| | | | | | | | | 8.10 | (1H) |
| | | | | | | | | 10.0–11.0 | (1H) |
| 19 | (18) | $CF_3$ | Cl | $O^nC_4H_9$ | $NHSO_2CH_3$ | $CH_3$ | 3100 | 0.8–1.8 | (4H) |
| | | | | | | | 1720 | 1.00 | (3H) |
| | | | | | | | 1690 | 1.70 | (3H) |
| | | | | | | | 1600 | 3.30 | (3H) |
| | | | | | | | 1250 | 4.35 | (2H) |
| | | | | | | | 1130 | 4.85 | (1H) |
| | | | | | | | | 6.50 | (1H) |
| | | | | | | | | 7.1–7.8 | (3H) |
| | | | | | | | | 7.90 | (1H) |
| | | | | | | | | 11.4–11.8 | (1H) |
| 20 | (19) | $CF_3$ | Cl | $OCH_3$ | $SCH_3$ | $CH_3$ | 1725 | 1.60 | (3H) |
| | | | | | | | 1705 | 2.27 | (3H) |
| | | | | | | | 1675 | 3.88 | (3H) |
| | | | | | | | 1595 | 4.78 | (1H) |
| | | | | | | | 1490 | 6.40–6.60 | (2H) |
| | | | | | | | 1320 | 7.07 | (1H) |
| | | | | | | | 1125 | 7.50 | (1H) |
| | | | | | | | | 7.70–7.90 | (2H) |
| 21 | (20) | $CF_3$ | Cl | $SCH_3$ | $OCH_3$ | $CH_3$ | 1755 | 1.72 | (3H) |
| | | | | | | | 1740 | 2.43 | (3H) |
| | | | | | | | 1675 | 3.73 | (3H) |
| | | | | | | | 1630 | 4.80 | (3H) |
| | | | | | | | 1590 | 6.40–6.60 | (2H) |
| | | | | | | | 1490 | 7.07 | (1H) |
| | | | | | | | 1320 | 7.50 | (1H) |
| | | | | | | | 1125 | 7.70–7.90 | (2H) |
| 22 | (21) | $CF_3$ | Cl | $OCH_3$ | $SCH_2COOC_2H_5$ | $CH_3$ | 1730 | 1.23 | (3H) |
| | | | | | | | 1720 | 1.61 | (3H) |
| | | | | | | | 1700 | 3.63 | (2H) |
| | | | | | | | 1595 | 3.90 | (3H) |
| | | | | | | | 1490 | 4.13 | (2H) |
| | | | | | | | 1320 | 4.83 | (1H) |
| | | | | | | | 1125 | 6.43 6.60 | (2H) |
| | | | | | | | | 7.08 | (1H) |
| | | | | | | | | 7.53 | (1H) |
| | | | | | | | | 7.70–7.94 | (2H) |
| 23 | (22) | $CF_3$ | Cl | $SCH_2COOC_2H_5$ | $OCH_3$ | $CH_3$ | 1750 | 1.27 | (3H) |
| | | | | | | | 1735 | 1.73 | (3H) |
| | | | | | | | 1690 | 3.70 | (3H) |
| | | | | | | | 1635 | 3.77 | (3H) |
| | | | | | | | 1590 | 4.18 | (2H) |
| | | | | | | | 1490 | 4.80 | (1H) |
| | | | | | | | 1320 | 6.37–6.60 | (2H) |
| | | | | | | | 1130 | 7.08 | (1H) |
| | | | | | | | | 7.53 | (1H) |
| | | | | | | | | 7.73 | (1H) |
| | | | | | | | | 7.88 | (1H) |
| 24 | (23) | $CF_3$ | Cl | NH—C₆H₅ | $OCH_3$ | $CH_3$ | 3350 | 1.72 | (3H) |
| | | | | | | | 1750 | 3.80 | (3H) |
| | | | | | | | 1655 | 5.00 | (1H) |
| | | | | | | | 1590 | 6.53–6.70 | (2H) |
| | | | | | | | 1490 | 7.00–7.86 | (8H) |
| | | | | | | | 1320 | 8.27 | (1H) |
| | | | | | | | 1125 | 10.00 | (1H) |
| 25 | (24) | $CF_3$ | Cl | $OCH_3$ | $OCH_2CF_3$ | $CH_3$ | 1770 | 1.72 | (3H) |
| | | | | | | | 1725 | 3.87 | (3H) |
| | | | | | | | 1595 | 4.50 | (2H) |
| | | | | | | | 1490 | 4.83 | (1H) |
| | | | | | | | 1320 | 6.47 6.63 | (2H) |

TABLE 1-continued
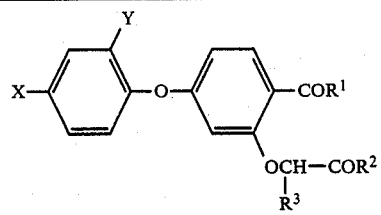
| Example No. | Compound No. | X | Y | R¹ | R² | R³ | IR $\nu(cm^{-1})$ | NMR in CDCl$_3$ $\delta$(ppm) | |
|---|---|---|---|---|---|---|---|---|---|
| | | | | | | | 1125 | 7.07 | (1H) |
| | | | | | | | | 7.50 | (1H) |
| | | | | | | | | 7.70–7.90 | (2H) |
| 26 | (25) | CF$_3$ | Cl | OCH$_2$CF$_3$ | OCH$_3$ | CH$_3$ | 1750 | 1.63 | (3H) |
| | | | | | | | 1595 | 3.67 | (3H) |
| | | | | | | | 1490 | 4.60 | (2H) |
| | | | | | | | 1320 | 4.73 | (1H) |
| | | | | | | | 1130 | 6.37–6.60 | (2H) |
| | | | | | | | | 7.07 | (1H) |
| | | | | | | | | 7.50 | (1H) |
| | | | | | | | | 7.70 | (1H) |
| | | | | | | | | 7.87 | (1H) |
| 27 | (26) | CF$_3$ | Cl | CN | OCH$_3$ | CH$_3$ | 2200 | 1.57 | (3H) |
| | | | | | | | 1750 | 3.60 | (3H) |
| | | | | | | | 1590 | 4.70 | (1H) |
| | | | | | | | 1490 | 6.27–6.53 | (2H) |
| | | | | | | | 1320 | 6.93 | (1H) |
| | | | | | | | 1125 | 7.47 | (1H) |
| | | | | | | | | 7.67 | (1H) |
| | | | | | | | | 7.83 | (1H) |
| 28 | (27) | CF$_3$ | Cl | CH$_3$ | OCH$_3$ | CH$_3$ | 1755 | 1.68 | (3H) |
| | | | | | | | 1670 | 2.67 | (3H) |
| | | | | | | | 1590 | 3.73 | (3H) |
| | | | | | | | 1490 | 4.83 | (1H) |
| | | | | | | | 1320 | 6.40–6.60 | (2H) |
| | | | | | | | 1130 | 7.07 | (1H) |
| | | | | | | | | 7.50 | (1H) |
| | | | | | | | | 7.70–7.83 | (2H) |
| 29 | (28) | CF$_3$ | Cl | CH$_3$ | OC$_2$H$_5$ | CH$_3$ | 1750 | 1.20 | (3H) |
| | | | | | | | 1670 | 1.65 | (3H) |
| | | | | | | | 1590 | 2.67 | (3H) |
| | | | | | | | 1490 | 4.15 | (3H) |
| | | | | | | | 1320 | 4.76 | (1H) |
| | | | | | | | 1130 | 6.38–6.60 | (2H) |
| | | | | | | | | 7.03 | (1H) |
| | | | | | | | | 7.47 | (1H) |
| | | | | | | | | 7.67–7.82 | (2H) |
| 30 | (29) | CF$_3$ | Cl | CH$_3$ OCHCOOCH$_3$ | OCH$_3$ | CH$_3$ | 1755 | 1.52 | (3H) |
| | | | | | | | 1740 | 1.58 | (3H) |
| | | | | | | | 1595 | 3.63 | (3H) |
| | | | | | | | 1490 | 3.70 | (3H) |
| | | | | | | | 1320 | 4.67 | (1H) |
| | | | | | | | 1125 | 5.25 | (1H) |
| | | | | | | | | 6.40–6.60 | (2H) |
| | | | | | | | | 7.03 | (1H) |
| | | | | | | | | 7.47 | (1H) |
| | | | | | | | | 7.70 | (1H) |
| | | | | | | | | 7.90 | (1H) |
| 31 | (30) | CF$_3$ | Cl | OCH$_3$ | OCH$_2$CH$_2$CH$_2$CH$_3$ | CH$_3$ | 1750 | 0.33–1.43 | (7H) |
| | | | | | | | 1730 | 1.53 | (3H) |
| | | | | | | | 1595 | 3.75 | (3H) |
| | | | | | | | 1490 | 4.00 | (2H) |
| | | | | | | | 1320 | 4.57 | (1H) |
| | | | | | | | 1125 | 6.37–6.53 | (2H) |
| | | | | | | | | 6.96 | (1H) |
| | | | | | | | | 7.40 | (1H) |
| | | | | | | | | 7.60–7.80 | (2H) |

TABLE 1-continued

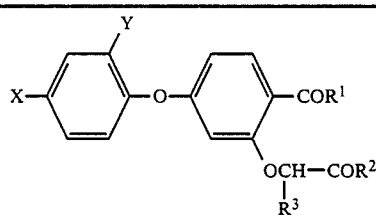

| Example No. | Compound No. | X | Y | R¹ | R² | R³ | IR $\nu$(cm$^{-1}$) | NMR $^{in}$CDCl$_3$ $\delta$(ppm) |
|---|---|---|---|---|---|---|---|---|
| 32 | (31) | CF$_3$ | Cl | OCH$_3$ | NHCH(CH$_3$)$_2$ | CH$_3$ | 3320 1710 1680 1595 1490 1320 1130 | 1.10–1.30 (6H) 1.63 (3H) 3.86 (3H) 3.93–4.90 (2H) 6.37–7.27 (3H) 7.53 (1H) 7.76–7.93 (2H) 7.96–8.33 (1H) |

FORMULATION EXAMPLE

One part of the active compound of this invention was added to 5,000 parts of a mixture of acetone and water (1:1 by volume), and 2.6 parts of a nonionic surfactant (Sorpol 2680, tradename) was added to form a solution.

TEST EXAMPLE 1

A solution of the active compound of the invention was prepared in accordance with the above Formulation Example.

Seeds of plants were sown in the soil, and after germination, cultivated for 2 to 3 weeks.

The prepared solution was applied to these plants at the rate of application indicated in Tables 2 and 3. Thereafter, the plants were continued to be cultivated for 3 weeks without applying the above solution. The results are given in Table 2.

TEST EXAMPLE 2

Seeds of plants to be evaluated were sown in the soil, and on the second day after sowing, were treated as follows and the growth of the plants was observed for 3 weeks.

A solution of the active compound of the invention was uniformly applied at the rate of application indicated in Table 3 to the surface of the soil after the sowing. Thereafter, the plants were continued to be cultivated without applying the active compound. The results are shown in Table 3.

The letters given in the column of "Plant" in Tables 2 to 8 represent the following plants.

a: *Ipomoea purpurea*
b: *Datula stramonium*
c: *Polygonum convolvulus*
d: *Ambrosia artemisiaefolia*
e: *Chenopodium album*
f: *Amaranthus retroflexas*
g: *Desmodium tortuosum*
h: *Abutilon theophrasti*
i: *Solanum nigrum*
j: *Xanthium strumarium*
k: soybean
l: corn
m: *Erigeron annuus*
n: *Digitaria adscendens*
o: *Setaria viridis*
p: *Sorghum halepense*
q: *Cyperus rotundus*
r: *Setaria faberi*
s: *Echinochloa crus-galli*
t: *Avera fatua*
u: *Cheropdium album*
v: *Sida spinosa*
w: *Polygonum hydropiper*
x: *Desmodium tortuosum*
y: *Portulaca oleracea*
z: *Cyperus microiria*

TABLE 2

| Compound No. | Rate of application (kg/ha) | a | b | c | d | e | f | g | h | i | j | k | l |
|---|---|---|---|---|---|---|---|---|---|---|---|---|---|
| (1) | 0.5 | 5 | 5 | 5 | 5 | 5 | 5 | 5 | 5 | 5 | 3 | 2 | 0 |
|  | 0.125 | 5 | 5 | 5 | 2 | 3 | 4 | 3 | 5 | 5 | 2 | 1 | 0 |
| (2) | 0.5 | 5 | 5 | 5 | 5 | 5 | 5 | 5 | 5 | 5 | 4 | 2 | 0 |
|  | 0.125 | 5 | 5 | 5 | 3 | 4 | 4 | 4 | 5 | 5 | 2 | 1 | 0 |
| (3) | 1 | — | — | — | — | 2 | 1 | 2 | 5 | 3 | 2 | 1 | 0 |
| (5) | 1 | — | — | — | — | 2 | 1 | 2 | 5 | 2 | 1 | 1 | 0 |
| (6) | 1 | — | — | — | — | 3 | 1 | 2 | 4 | 3 | 5 | 2 | 0 |
| (7) | 1 | — | — | — | — | 2 | 1 | 2 | 5 | 1 | 2 | 1 | 0 |
| (8) | 1 | — | — | — | — | 1 | 2 | 3 | 4 | 2 | 5 | 0 | 0 |
| (9) | 0.5 | — | — | — | — | 5 | 3 | 5 | 5 | 5 | 3 | 2 | 0 |
| (10) | 0.5 | — | — | — | — | 5 | 4 | 5 | 5 | 5 | 3 | 2 | 0 |
| (11) | 1 | — | — | — | — | 2 | 2 | 3 | 5 | 5 | 2 | 0 | 0 |
| (12) | 1 | — | — | — | — | 2 | 2 | 2 | 5 | 4 | 2 | 0 | 0 |
| (13) | 0.5 | — | — | — | — | 4 | 3 | 4 | 5 | 5 | 3 | 1 | 0 |
| (14) | 1 | — | — | — | — | 4 | 3 | 2 | 3 | 2 | 2 | 0 | 0 |

TABLE 2-continued

| Compound No. | Rate of application (kg/ha) | Plant a | b | c | d | e | f | g | h | i | j | k | l |
|---|---|---|---|---|---|---|---|---|---|---|---|---|---|
| (15) | 1 | — | — | — | — | 4 | 3 | 3 | 4 | 4 | 3 | 0 | 0 |
| (16) | 1 | — | — | — | — | 3 | 3 | 3 | 4 | 4 | 3 | 0 | 0 |
| (17) | 1 | — | — | — | — | 2 | 2 | 2 | 3 | 3 | 2 | 0 | 0 |
| (18) | 1 | — | — | — | — | 3 | 2 | 3 | 3 | 4 | 3 | 0 | 0 |
| (19) | 0.5 | — | — | — | — | 5 | 5 | 5 | 5 | 5 | 3 | 2 | 0 |
|  | 0.125 | — | — | — | — | 3 | 5 | 4 | 5 | 5 | 2 | 1 | 0 |
| (20) | 0.5 | — | — | — | — | 2 | 4 | 2 | 5 | 4 | 2 | 1 | 0 |
| (21) | 0.5 | — | — | — | — | 4 | 5 | 5 | 5 | 5 | 3 | 2 | 0 |
|  | 0.125 | — | — | — | — | 4 | 2 | 4 | 5 | 4 | 2 | 1 | 0 |
| (22) | 0.5 | — | — | — | — | 2 | 1 | 3 | 4 | 2 | 1 | 1 | 0 |
| (23) | 0.5 | — | — | — | — | 3 | 2 | 2 | 4 | 2 | 2 | 1 | 0 |
| (24) | 0.5 | — | — | — | — | 5 | 4 | 5 | 5 | 5 | 2 | 2 | 0 |
|  | 0.125 | — | — | — | — | 3 | 2 | 4 | 5 | 3 | 1 | 1 | 0 |
| (25) | 0.5 | — | — | — | — | 2 | 2 | 1 | 5 | 2 | 1 | 1 | 0 |
| (26) | 0.5 | — | — | — | — | 2 | 2 | 2 | 4 | 2 | 1 | 0 | 0 |
| (27) | 0.5 | — | — | — | — | 3 | 3 | 4 | 5 | 5 | 5 | 2 | 0 |
| (28) | 0.5 | — | — | — | — | 2 | 3 | 4 | 5 | 4 | 5 | 2 | 0 |
| (29) | 0.5 | — | — | — | — | 2 | 4 | 3 | 5 | 4 | 1 | 1 | 0 |
| (30) | 0.5 | — | — | — | — | 4 | 5 | 5 | 5 | 5 | 4 | 2 | 0 |
| (31) | 0.5 | — | — | — | — | 2 | 2 | 3 | 4 | 4 | 2 | 1 | 0 |

TABLE 3

| Compound No. | Rate of application (kg/ha) | Plant m | f | i | a | g | k | l |
|---|---|---|---|---|---|---|---|---|
| (1) | 0.5 | 5 | 5 | 3 | 4 | 5 | 0 | 0 |
|  | 0.125 | 5 | 5 | 1 | 4 | 5 | 0 | 0 |
| (2) | 0.5 | 5 | 5 | 4 | 5 | 5 | 0 | 0 |
|  | 0.125 | 5 | 5 | 1 | 5 | 5 | 0 | 0 |

TEST EXAMPLES 3-19 AND TEST COMPARATIVE EXAMPLES 1-6

In each run, each of the phenoxycarboxylates shown in Table 4 alone or with each of the N-phosphonomethylglycine derivatives shown in Table 4 (in the indicated mixing ratios) was dissolved in 16 parts by volume of a mixture of water and acetone (1:1 by volume; containing 0.05% of a nonionic surfactant, SORPOL-2680) to prepare a spray solution. The amounts of the herbicidal compounds were such that the rates of application were as shown in Table 4.

The plants tested were grown in vinyl resin pots (diameter 10 cm) filled with soil in a greenhouse for 2 to 3 weeks after germination from seeds or tubers.

The spray solution was applied to the plants so that the total volume sprayed became 4 cc/100 cm$^2$, and the herbicidal activity was examined.

The results are shown in Table 4.

TABLE 4

| No. | Compound No. | Rate of application (kg/ha) | Mixing ratio (I:II) | Days after the spraying | Plant n | o | p | q | e | f | g | h | i |
|---|---|---|---|---|---|---|---|---|---|---|---|---|---|
| TEST COMPARATIVE EXAMPLE 1 | (67) | 2 | — | 3 | 0 | 0 | 0 | 0 | 0 | 0 | 0 | 0 | 0 |
|  |  |  |  | 7 | 3 | 2 | 2 | 0 | 2 | 2 | 3 | 2 | 2 |
|  |  |  |  | 14 | 5 | 5 | 5 | 0 | 5 | 3 | 5 | 5 | 4 |
| TEST COMPARATIVE EXAMPLE 2 | (67) | 1.5 | — | 3 | 0 | 0 | 0 | 0 | 0 | 0 | 0 | 0 | 0 |
|  |  |  |  | 7 | 3 | 2 | 2 | 0 | 2 | 2 | 3 | 2 | 1 |
|  |  |  |  | 14 | 5 | 5 | 5 | 0 | 5 | 3 | 5 | 5 | 4 |
| TEST COMPARATIVE EXAMPLE 3 | (67) | 1 | — | 3 | 0 | 0 | 0 | 0 | 0 | 0 | 0 | 0 | 0 |
|  |  |  |  | 7 | 3 | 2 | 2 | 0 | 1 | 1 | 2 | 1 | 1 |
|  |  |  |  | 14 | 5 | 5 | 5 | 0 | 5 | 3 | 4 | 4 | 4 |
| TEST COMPARATIVE EXAMPLE 4 | (67) | 0.75 | — | 3 | 0 | 0 | 0 | 0 | 0 | 0 | 0 | 0 | 0 |
|  |  |  |  | 7 | 3 | 1 | 2 | 0 | 0 | 1 | 2 | 1 | 1 |
|  |  |  |  | 14 | 5 | 5 | 5 | 0 | 1 | 3 | 4 | 3 | 4 |
| TEST COMPARATIVE EXAMPLE 5 | (67) | 0.5 | — | 3 | 0 | 0 | 0 | 0 | 0 | 0 | 0 | 0 | 0 |
|  |  |  |  | 7 | 2 | 1 | 1 | 0 | 0 | 0 | 1 | 1 | 1 |
|  |  |  |  | 14 | 5 | 5 | 5 | 0 | 1 | 1 | 3 | 3 | 3 |
| TEST EXAMPLE 3 | (2) (67) | 0.5 1.5 | 1:3 | 3 | 2 | 2 | 2 | 3 | 3 | 2 | 2 | 3 | 4 |
|  |  |  |  | 7 | 4 | 4 | 4 | 4 | 5 | 5 | 5 | 5 | 5 |
|  |  |  |  | 14 | 5 | 5 | 5 | 5 | 5 | 5 | 5 | 5 | 5 |
| TEST EXAMPLE 4 | (2) (67) | 0.25 1.25 | 1:5 | 3 | 2 | 2 | 2 | 2 | 2 | 2 | 2 | 3 | 4 |
|  |  |  |  | 7 | 4 | 4 | 4 | 3 | 4 | 5 | 4 | 5 | 5 |
|  |  |  |  | 14 | 5 | 5 | 5 | 3 | 5 | 5 | 5 | 5 | 5 |
| TEST EXAMPLE 5 | (2) (67) | 0.05 0.95 | 1:19 | 3 | 1 | 1 | 1 | 1 | 1 | 1 | 1 | 2 | 3 |
|  |  |  |  | 7 | 4 | 3 | 4 | 1 | 2 | 1 | 3 | 5 | 5 |
|  |  |  |  | 14 | 5 | 5 | 5 | 1 | 5 | 4 | 3 | 5 | 5 |
| TEST EXAMPLE 6 | (2) (67) | 0.125 0.875 | 1:7 | 3 | 1 | 1 | 1 | 1 | 2 | 2 | 2 | 3 | 4 |
|  |  |  |  | 7 | 5 | 4 | 4 | 1 | 3 | 3 | 4 | 5 | 5 |
|  |  |  |  | 14 | 5 | 5 | 5 | 2 | 5 | 4 | 5 | 5 | 5 |
| TEST EXAMPLE 7 | (2) (67) | 0.25 0.75 | 1:3 | 3 | 2 | 1 | 1 | 2 | 3 | 2 | 2 | 3 | 4 |
|  |  |  |  | 7 | 4 | 4 | 4 | 3 | 5 | 5 | 5 | 5 | 5 |
|  |  |  |  | 14 | 5 | 5 | 5 | 3 | 5 | 5 | 5 | 5 | 5 |
| TEST EXAMPLE 8 | (2) (67) | 0.5 0.5 | 1:1 | 3 | 2 | 2 | 2 | 2 | 3 | 3 | 2 | 3 | 4 |
|  |  |  |  | 7 | 4 | 4 | 4 | 3 | 5 | 5 | 5 | 5 | 5 |
|  |  |  |  | 14 | 5 | 5 | 5 | 3 | 5 | 5 | 5 | 5 | 5 |

TABLE 4-continued

| No. | Compound No. | Rate of application (kg/ha) | Mixing ratio (I:II) | Days after the spraying | Plant n | o | p | q | e | f | g | h | i |
|---|---|---|---|---|---|---|---|---|---|---|---|---|---|
| TEST EXAMPLE 9 | (2) (67) | 0.75 0.25 | 3:1 | 3 7 14 | 2 3 5 | 2 3 5 | 1 3 4 | 2 2 3 | 2 4 5 | 1 4 5 | 2 5 5 | 3 5 5 | 4 5 5 |
| TEST EXAMPLE 10 | (2) (67) | 0.875 0.125 | 7:1 | 3 7 14 | 2 3 4 | 2 2 5 | 1 3 5 | 2 3 3 | 2 5 5 | 2 5 5 | 3 5 5 | 3 5 5 | 4 5 5 |
| TEST EXAMPLE 11 | (2) (67) | 0.95 0.05 | 19:1 | 3 7 14 | 2 3 4 | 1 2 4 | 1 3 4 | 2 2 2 | 2 5 5 | 2 5 5 | 3 5 5 | 3 5 5 | 4 5 5 |
| TEST EXAMPLE 12 | (2) (67) | 0.25 0.5 | 1:2 | 3 7 14 | 2 4 5 | 1 4 5 | 1 4 5 | 2 2 2 | 2 5 5 | 2 5 5 | 2 5 5 | 3 5 5 | 4 5 5 |
| TEST EXAMPLE 13 | (2) (67) | 0.25 0.25 | 1:1 | 3 7 14 | 1 3 5 | 1 3 5 | 1 3 5 | 1 1 1 | 2 5 5 | 1 5 5 | 2 4 5 | 3 5 5 | 3 5 5 |
| TEST EXAMPLE 14 | (2) (67) | 0.5 — | — | 3 7 14 | 1 1 1 | 1 1 1 | 1 1 1 | 1 1 1 | 2 4 5 | 2 5 5 | 2 5 5 | 3 5 5 | 2 5 5 |
| TEST EXAMPLE 15 | (2) (67) | 0.25 — | — | 3 7 14 | 1 1 1 | 1 1 0 | 1 1 1 | 1 1 1 | 1 2 5 | 1 5 5 | 1 4 5 | 2 4 5 | 3 5 5 |
| TEST EXAMPLE 16 | (2) (67) | 0.125 — | — | 3 7 14 | 1 1 1 | 1 0 0 | 1 1 1 | 1 1 1 | 1 2 5 | 1 2 5 | 1 3 5 | 2 5 5 | 3 5 5 |
| TEST EXAMPLE 17 | (27) (67) | 0.25 0.75 | 1:3 | 3 7 14 | 2 4 5 | 1 3 5 | 1 3 5 | 1 1 1 | 2 3 5 | 1 2 5 | 2 3 5 | 3 5 5 | 2 4 5 |
| TEST EXAMPLE 18 | (27) | 0.75 0.25 | — | 3 7 14 | 1 1 0 | 1 1 1 | 1 1 1 | 1 0 0 | 1 2 2 | 1 2 2 | 1 2 3 | 2 5 5 | 2 3 3 |
| TEST COMPARATIVE EXAMPLE 6 | (51) | 1 | — | 3 7 14 | 0 3 5 | 0 2 5 | 0 2 5 | 0 0 0 | 0 0 4 | 0 0 4 | 0 1 4 | 0 2 4 | 0 2 4 |
| TEST EXAMPLE 19 | (2) (51) | 0.25 0.75 | 1:3 | 3 7 14 | 2 5 5 | 1 4 5 | 2 4 5 | 1 2 2 | 2 3 5 | 3 5 5 | 2 4 5 | 3 5 5 | 3 5 5 |

When the results of Test Examples 3 to 19 and Test Comparative Examples 1 to 6 are compared, it is found that the herbicidal compositions of this invention comprising the two types of herbicidal compounds indicated above exhibit herbicidal activity earlier and thus have better fast-acting efficacy than the N-phosphonomethylglycine derivatives alone.

The N-phosphonomethylglycine derivatives, used alone particularly in low dosages, have lowered heribicidal activity on broad-leaved weeds such as *Chenopodium album* and *Amaranthus retroflexas*, and 14 days after the spraying in the above tests, showed hardly any activity or showed only insufficient activity.

In contrast, the compositions of this invention, for example that used in Test Example 3, could kill all of the weeds shown in Table 4 within about 1 week. By applying a combination of the phenoxycarboxylate and the N-phosphonomethylglycine derivative, the herbicidal composition of this invention surprisingly showed increased fact-acting efficacy and a broadened heribicidal spectrum at low dosages as the synergistic effect of the combined use.

TEST EXAMPLES 20–24 AND TEST COMPARATIVE EXAMPLES 7–8

In each run, each of the phenoxycarboxylates shown in Table 4 alone or with each of the N-phosphonomethylglycine derivatives shown in Table 5 (in the indicated mixing ratios) was dissolved in 16 parts by volume of a mixture of water and acetone (1:1 by volume; containing 0.05% of a nonionic surfactant, SORPOL-2680) to prepare a spray solution. The amounts of the herbicidal compounds were such that the rates of application were as shown in Table 5.

The plants tested were grown in an outdoor test field for 2 to 3 weeks after germination from seeds or tubers.

The spray solution was applied to the plants so that the total volume sprayed became 400 cc/m$^2$. The herbicidal activity was examined, and the results are shown in Table 5.

TABLE 5

| No. | Compound No. | Rate of application (kg/ha) | Mixing ratio (I:II) | Days after the spraying | Plant n | r | p | s | t | z | q | e | u | a | b | i | v | h | w | x | j | f | y |
|---|---|---|---|---|---|---|---|---|---|---|---|---|---|---|---|---|---|---|---|---|---|---|---|
| TEST COMPARATIVE EXAMPLE 7 | (67) | 2 | — | 2 7 14 | 0 3 5 | 0 3 5 | 0 3 5 | 0 2 5 | 1 3 5 | 0 2 4 | 0 1 2 | 1 4 5 | 1 3 5 | 0 1 1 | 2 3 5 | 0 3 5 | 0 2 4 | 1 3 4 | 0 3 5 | 1 4 5 | 1 3 5 | 1 2 5 | 0 3 4 |
| TEST COMPARATIVE EXAMPLE 8 | (67) | 1 | — | 2 7 14 | 0 3 5 | 0 3 5 | 0 3 5 | 0 2 5 | 1 3 5 | 0 2 4 | 0 1 1 | 1 3 5 | 1 3 5 | 0 1 1 | 1 3 5 | 0 3 5 | 0 2 4 | 0 3 5 | 0 3 5 | 1 4 5 | 1 3 4 | 1 2 5 | 0 3 3 |
| TEST EXAMPLE 20 | (2) (67) | 0.5 1.5 | 1:3 | 2 7 14 | 2 4 5 | 2 4 5 | 2 4 5 | 1 3 5 | 2 4 5 | 2 4 5 | 2 4 5 | 4 5 5 | 4 5 5 | 4 5 5 | 4 5 5 | 3 5 5 | 4 5 5 | 4 5 5 | 3 5 5 | 3 5 5 | 4 5 5 | 5 5 5 | 4 5 5 |

TABLE 5-continued

| No. | Compound No. | Rate of application (kg/ha) | Mixing ratio (I:II) | Days after the spraying | Plant | | | | | | | | | | | | | | | | |
|---|---|---|---|---|---|---|---|---|---|---|---|---|---|---|---|---|---|---|---|---|---|
| | | | | | n | r | p | s | t | z | q | e | u | a | b | i | v | h | w | x | j | f | y |
| TEST EXAMPLE 21 | (2) (67) | 0.25 1 | 1:4 | 2 7 14 | 2 4 5 | 2 4 5 | 2 4 5 | 1 3 5 | 1 3 5 | 2 4 4 | 2 4 5 | 3 5 5 | 3 5 5 | 4 5 5 | 4 5 5 | 3 4 5 | 2 5 5 | 4 5 5 | 3 5 5 | 3 5 5 | 4 5 5 | 4 5 5 |
| TEST EXAMPLE 22 | (2) (67) | 0.25 0.75 | 1:3 | 2 7 14 | 2 4 5 | 2 4 5 | 2 4 5 | 1 3 5 | 1 3 5 | 2 4 4 | 2 4 5 | 3 5 5 | 3 5 5 | 4 5 5 | 4 5 5 | 3 4 5 | 2 5 5 | 4 5 5 | 3 5 5 | 3 5 5 | 4 5 5 | 4 5 5 |
| TEST EXAMPLE 23 | (2) (67) | 0.5 0.5 | 1:1 | 2 7 14 | 2 4 5 | 2 4 5 | 2 4 5 | 1 3 5 | 1 3 5 | 2 4 3 | 2 4 5 | 4 5 5 | 4 5 5 | 4 5 5 | 4 5 5 | 3 5 5 | 3 5 5 | 4 5 5 | 3 5 5 | 3 5 5 | 4 5 5 | 4 5 5 |
| TEST EXAMPLE 24 | (2) | 0.25 | — | 2 7 14 | 1 1 1 | 1 1 0 | 1 1 0 | 1 1 0 | 1 1 0 | 1 2 2 | 1 2 2 | 3 4 5 | 3 4 5 | 3 5 5 | 4 5 5 | 3 4 5 | 2 4 4 | 3 5 5 | 3 4 5 | 3 4 5 | 3 5 5 | 3 5 5 |

When the results obtained in Test Examples 20 to 24 and Comparative Test Examples 7 to 8 are compared, it is found that the compositions in accordance with this invention show much the same synergistic effects as indicated in Table 4.

The N-phosphonomethylglycine derivative is used as a non-selective herbicide Roundup ®. This herbicide has a slow-acting effect as shown in Test Comparative Examples 7 and 8 and its activity is insufficient against plants of the Family Convolvulaceae such as *Ipomoea purpures*, and plants of the Cyperaceae such as *Cyperus rotundus*. The herbicidal composition of this invention, however, overcomes this defect, and owing to its synergistic effect, can be used as an excellent non-selective herbicide with fast-acting efficacy and a broadened herbicidal spectrum at low dosages.

TEST EXAMPLES 25-39 AND TEST COMPARATIVE EXAMPLES 9-15

In each run, a spray solution was prepared by mixing methyl 2-[2-methoxycarbonyl-5-(2-chloro-4-trifluoromethylphenoxy)]phenoxypropionate (compound No. 2) and [(3-amino-3-carboxy)propyl-1]-methylphosphinic acid (compound No. 100) at a predetermined mixing ratio and dissolving the mixture in 16 parts by volume of a mixture of water and acetone (volume ratio 1:1; containing 0.05% of SORPOL-2680, a tradename for a nonionic surfactant) so as to provide a predetermined rate of application.

The test plants were obtained by sowing seeds or transplanting rhizomes in vinyl plastic pots (diameter 10 cm) filled with soil, and cultivating them in a greenhouse for 2 to 3 weeks after germination.

The spray solution was applied to the plants so that the total amount of spray was 4 cc/100 cm$^2$, and the herbicidal activity of the compounds was examined.

The results are shown in Tables 6 and 7.

TABLE 6

| Run | Compound No. | Rate of application (kg/ha) | Mixing ratio (I:III) | Days after treatment | Plant | | | | | | | |
|---|---|---|---|---|---|---|---|---|---|---|---|---|
| | | | | | n | o | p | e | f | g | h | i |
| TEST COMPARATIVE EXAMPLE 9 | (2) (100) | — 1 | — | 3 7 14 | 2 4 5 | 2 4 5 | 2 4 5 | 3 4 5 | 1 3 5 | 2 4 5 | 2 3 5 | 2 4 5 |
| TEST COMPARATIVE EXAMPLE 10 | (2) (100) | — 0.75 | — | 3 7 14 | 2 4 5 | 2 4 5 | 2 4 5 | 3 4 5 | 1 4 5 | 2 4 5 | 2 3 4 | 2 4 5 |
| TEST COMPARATIVE EXAMPLE 11 | (2) (100) | — 0.5 | — | 3 7 14 | 2 4 5 | 2 4 5 | 1 3 5 | 2 3 4 | 1 3 5 | 2 4 4 | 1 2 5 | 1 3 5 |
| TEST COMPARATIVE EXAMPLE 12 | (2) (100) | — 0.25 | — | 3 7 14 | 1 3 4 | 1 3 4 | 1 2 2 | 1 3 3 | 0 1 1 | 1 4 5 | 0 2 2 | 0 2 4 |
| TEST COMPARATIVE EXAMPLE 13 | (2) (100) | — 0.125 | — | 3 7 14 | 1 3 4 | 1 3 4 | 1 2 2 | 1 1 1 | 0 1 1 | 1 4 4 | 0 2 2 | 0 2 3 |
| TEST EXAMPLE 25 | (2) (100) | 0.05 0.95 | 1:19 | 3 7 14 | 4 4 5 | 3 5 5 | 3 5 5 | 3 4 5 | 4 4 5 | 4 4 5 | 4 4 5 | 4 4 5 |
| TEST EXAMPLE 26 | (2) (100) | 0.125 0.875 | 1:7 | 3 7 14 | 4 4 5 | 3 5 5 | 2 4 5 | 3 5 5 | 4 4 5 | 4 4 5 | 4 4 5 | 4 5 5 |
| TEST EXAMPLE 27 | (2) (100) | 0.25 0.75 | 1:3 | 3 7 14 | 4 5 5 | 3 5 5 | 2 5 5 | 4 5 5 | 4 5 5 | 4 5 5 | 4 5 5 | 5 5 5 |
| TEST EXAMPLE 28 | (2) (100) | 0.5 0.5 | 1:1 | 3 7 14 | 4 5 5 | 4 5 5 | 3 4 5 | 3 5 5 | 3 4 5 | 3 4 5 | 4 5 5 | 4 5 5 |
| TEST EXAMPLE 29 | (2) (100) | 0.75 0.25 | 3:1 | 3 7 14 | 4 5 5 | 3 4 4 | 3 4 5 | 4 5 5 | 4 5 5 | 3 4 5 | 4 5 5 | 4 5 5 |
| TEST EXAMPLE 30 | (2) (100) | 0.875 0.125 | 7:1 | 3 7 | 4 4 | 3 5 | 2 3 | 4 5 | 4 5 | 3 4 | 4 5 | 5 5 |

TABLE 6-continued

| Run | Compound No. | Rate of application (kg/ha) | Mixing ratio (I:III) | Days after treatment | Plant | | | | | | | |
|---|---|---|---|---|---|---|---|---|---|---|---|---|
| | | | | | n | o | p | e | f | g | h | i |
| | | | | 14 | 5 | 5 | 4 | 5 | 5 | 5 | 5 | 5 |
| TEST EXAMPLE 31 | (2) (100) | 0.95 0.05 | 19:1 | 3 7 14 | 4 4 4 | 2 3 3 | 2 3 4 | 4 5 5 | 4 5 5 | 4 5 5 | 4 5 5 | 4 5 5 |
| TEST EXAMPLE 32 | (2) (100) | 0.25 0.5 | 1:2 | 3 7 14 | 4 4 5 | 4 5 5 | 2 4 5 | 3 5 5 | 3 4 5 | 3 5 5 | 4 5 5 | 4 5 5 |
| TEST EXAMPLE 33 | (2) (100) | 0.25 0.25 | 1:1 | 3 7 14 | 4 4 5 | 2 4 5 | 2 3 4 | 3 5 5 | 2 5 5 | 3 5 5 | 4 5 5 | 3 5 5 |
| TEST EXAMPLE 34 | (2) (100) | 0.125 0.375 | 1:3 | 3 7 14 | 3 4 5 | 3 5 5 | 2 5 5 | 4 5 5 | 4 5 5 | 4 5 5 | 4 5 5 | 4 5 5 |
| TEST EXAMPLE 35 | (2) (100) | 0.125 0.125 | 1:1 | 3 7 14 | 4 4 4 | 1 3 5 | 2 3 4 | 2 4 5 | 3 4 5 | 4 5 5 | 4 5 5 | 4 5 4 |
| TEST EXAMPLE 36 | (2) (100) | 0.063 0.187 | 1:3 | 3 7 14 | 3 4 5 | 2 3 5 | 2 4 4 | 2 4 5 | 2 3 4 | 3 5 5 | 4 5 5 | 3 4 4 |

TABLE 7

| Run | Compound No. | Rate of application (kg/ha) | Mixing ratio (I:III) | Days after treatment | Plant | | | |
|---|---|---|---|---|---|---|---|---|
| | | | | | z | a | b | w |
| TEST COMPARATIVE EXAMPLE 14 | (2) (100) | — 1 | — | 5 10 | 1 2 | 1 2 | 2 4 | 2 4 |
| TEST COMPARATIVE EXAMPLE 15 | (2) (100) | — 0.5 | — | 5 10 | 0 0 | 1 2 | 1 2 | 1 2 |
| TEST EXAMPLE 37 | (2) (100) | 0.25 0.75 | 1:3 | 5 10 | 4 5 | 5 5 | 5 5 | 4 5 |
| TEST EXAMPLE 38 | (2) (100) | 0.125 0.375 | 1:3 | 5 0 | 3 5 | 5 5 | 5 5 | 4 5 |
| TEST EXAMPLE 39 | (2) (100) | 0.125 — | — | 5 10 | 2 2 | 4 5 | 4 5 | 2 4 |

A comparison of the results of Test Examples 25 to 39 with the results of Comparative Test Comparative Examples 9 to 15 shows that the herbicidal composition of this invention exhibits its herbicidal activity earlier, and has faster efficacy, than the compound 100 or compound 2 singly used.

When compound 100 is singly used, its herbicidal activity on broad-leaved weeds such as *Polygonum convolvulus*, *Amaranthus retroflexas* and *Abutilon theophrasti* is reduced at low dosages. In contrast, the herbicidal composition of this invention overcomes this defect and shows sufficient herbicidal activity, as shown in Table 6. Furthermore, as shown in Table 7, the herbicidal composition of this invention shows a marked efficacy on *Cyperus microiria*, *Ipomoea purpurea* and *Datula stramonium*.

TEST EXAMPLES 40-41 AND TEST COMPARATIVE EXAMPLES 16-17

In Test Example 25 and Test Comparative Example 9, ammonium [(3-amino-3-carboxy)-propyl-1]-methyl-phosphinate (compound 103) was used instead of [(3-amino-3-carboxy)-propyl-1]-methylphosphinic acid (compound 100). Otherwise, a spray solution was prepared, and the herbicidal activity of the compounds was examined, in the same way as in these examples. The results are shown in Table 8.

TABLE 8

| Run | Compound No. | Rate of application (kg/ha) | Mixing ratio (I:III) | Days after treatment | Plant | | | | | | | |
|---|---|---|---|---|---|---|---|---|---|---|---|---|
| | | | | | n | o | p | e | f | g | h | i |
| TEST COMPARATIVE EXAMPLE 16 | (2) (103) | — 1 | — | 3 7 14 | 2 4 5 | 2 4 5 | 1 4 5 | 1 3 5 | 2 4 5 | 2 4 5 | 1 5 5 | 1 4 5 |
| TEST COMPARATIVE EXAMPLE 17 | (2) (103) | — 0.5 | — | 3 7 14 | 2 4 5 | 2 4 5 | 1 4 4 | 1 3 5 | 0 2 5 | 2 4 5 | 1 3 4 | 0 2 4 |
| TEST EXAMPLE 40 | (2) (103) | 0.25 0.75 | 1:3 | 3 7 14 | 3 5 5 | 3 5 5 | 2 5 5 | 3 4 5 | 2 5 5 | 3 5 5 | 3 5 5 | 3 5 5 |
| TEST | (2) | 0.125 | 1:3 | 3 | 3 | 3 | 2 | 2 | 3 | 3 | 3 | 2 |

TABLE 8-continued

| Run | Compound No. | Rate of application (kg/ha) | Mixing ratio (I:III) | Days after treatment | Plant n | o | p | e | f | g | h | i |
|---|---|---|---|---|---|---|---|---|---|---|---|---|
| EXAMPLE 41 | (103) | 0.375 | | 7 | 4 | 4 | 4 | 3 | 4 | 4 | 5 | 5 |
| | | | | 14 | 5 | 5 | 5 | 5 | 5 | 5 | 5 | 5 |

What is claimed is:

1. A phenoxycarboxylic acid represented by the following formula (I)

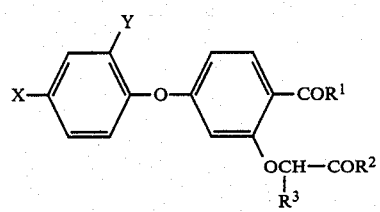

wherein X and Y are identical or different and each represents a hydrogen atom, a halogen atom, —CF$_3$, or an alkyl group having 1 to 5 carbon atoms; R$^1$ and R$^2$ are identical or different and each represents an alkyl group having 1 to 5 carbon atoms which may be substituted by an alkoxycarbonyl group having 2 to 6 carbon atoms, a cyano group, an alkylthio group having 1 to 5 carbon atoms which may be substituted by an alkoxycarbonyl group having 2 to 6 carbon atoms, a group of the formula —OR$^4$ in which R$^4$ is a hydrogen atom, an alkyl group having 1 to 5 carbon atoms, or a trifluoroalkyl group, or a group of the formula

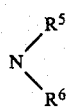

in which R$^5$ and R$^6$ are identical or different and each represents a hydrogen atom, an alkyl group having 1 to 5 carbon atoms, an alkylsulfonyl group having 1 to 5 carbon atoms, or a phenyl group; and R$^3$ represents a hydrogen atom or an alkyl group having 1 to 5 carbon atoms, or a salt of said compound in which R$^4$ is a hydrogen atom.

2. The compound of claim 1 wherein X is —CF$_3$.

3. The compound of claim 1 wherein Y is a halogen atom.

4. The compound of claim 1 wherein R$^1$ is an alkyl group having 1 to 5 carbon atoms which may be substituted by an alkoxycarbon group having 2 to 6 carbon atoms.

5. The compound of claim 1 wherein R$^1$ is —OR$^4$ and R$^4$ is an alkyl group having 1 to 5 carbon atoms, or a trifluoroalkyl group.

6. The compound of claim 1 wherein R$^2$ is an alkylthio group having 1 to 5 carbon atoms, which may be substituted by an alkoxycarbonyl group having 2 to 6 carbon atoms.

7. The compound of claim 1 wherein R$^2$ is —OR$^4$ and R$^4$ is an alkyl group having 1 to 5 carbon atoms or a trifluoroalkyl group.

8. The compound of claim 1 wherein R$^3$ is an alkyl group having 1 to 5 carbon atoms.

9. A herbicidal composition comprising a herbicidally effective amount of a compound of claim 1 as an active ingredient and a carrier and/or a surfactant.

10. A method of eradicating broad-leaved weeds, which comprising applying a compound of claim 1 or a herbicidal composition containing the compound of formula (I) to a locus where broad-leaved weeds are growing or are likely to grow in an amount effective for eradicating the weeds.

11. The method of claim 10 wherein the locus is a locus where a crop is cultivated, and the crop is either a broad-leaved plant or a narrow-leaved plant.

12. The method of claim 10 wherein the compound of formula (I) or a herbicidal composition containing the compound of formula (I) is applied to a locus where broad-leaved weeds are likely to grow before emergence of the weeds, and the locus is a locus where a broad-leaved plant is cultivated.

13. A herbicidal composition comprising as a herbicidal ingredient a combination of herbicidally effective amounts of a compound of claim 1 and a compound represented by the following formula (II)

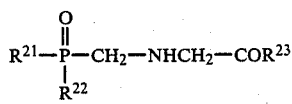

wherein R$^{21}$ and R$^{22}$ are identical or different and each represents —OH or a group of the formula —OR$^{24}$, R$^{23}$ represents —OH, a group of the formula —OR$^{24}$ or a group of the formula —NR$^{25}$R$^{26}$ in which R$^{24}$ is an alkyl group having 1 to 5 carbon atoms, a cyclohexyl group, a haloalkyl group having 1 to 5 carbon atoms, an alkenyl group having 2 to 5 carbon atoms or an alkoxy-alkyl, haloalkoxy-alkyl or alkoxy-alkoxy-alkyl group in which each of the alkoxy, haloalkoxy and alkyl moieties has 1 to 5 carbon atoms, or a phenoxy group, R$^{25}$ and R$^{26}$ are identical or different and each represents a hydrogen atom, an alkyl group having 1 to 5 carbon atoms, a hydroxyalkyl group having 1 to 5 carbon atoms, an alkenyl group having 2 to 5 carbon atoms and, R$^{25}$ and R$^{26}$, taken together with the nitrogen atom to which they are attached, form a morpholino, piperidino or pyrrolidino group, or an acid addition salt thereof or a salt thereof with a base, and a carrier and/or a surfactant.

14. The composition of claim 13 wherein the weight ratio of the compound of claim 1 to the compound of formula (II) is from 1:50 to 50:1.

15. A method of eradicating weeds, which comprises applying the compound of formula (I) and the compound of formula (II), simultaneously or successively, to a locus where weeds are growing in an amount effective for eradicating the weeds.

16. The method of claim 15 wherein the locus is a locus for cultivating crop, and the compound of formula (I) and the compound of formula (II) are applied to the locus before emergence of the crop.

17. A herbicidal composition which comprises as a herbicidal ingredient a combination of herbicidally effective amounts of the compound of claim 1 and a compound represented by the following formula (III)

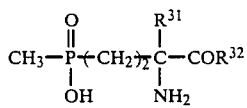

wherein $R^{31}$ represents a hydrogen atom or an alkyl group having 1 to 4 carbon atoms, $R^{32}$ represents —OH, —NH$_2$, —NHNH$_2$, —NHC$_6$H$_5$, or an alkoxy group having 1 to 12 carbon atoms which may be substituted by —OH, or an acid addition salt thereof or a salt thereof with a base, and a carrier and/or a surfactant.

18. The composition of claim 17 wherein the weight ratio of the compound of claim 1 to the compound of formula (III) is from 1:50 to 50:1.

19. A method of eradicating weeds, which comprises applying the compound of formula (I) and the compound of formula (III), simultaneously or successively, to a locus where weeds are growing in an amount effective for eradicating the weeds.

20. The method of claim 18 wherein the locus is a locus for cultivating crop, and the compound of formula (I) and the compound of formula (III) are applied to the locus before emergence of the crop.

* * * * *